(12) United States Patent
Noh et al.

(10) Patent No.: US 10,056,552 B2
(45) Date of Patent: Aug. 21, 2018

(54) COMPOUND FOR ORGANIC LIGHT-EMITTING DEVICE, CROSS-LINKED MATERIAL THEREOF, AND ORGANIC LIGHT-EMITTING DEVICE INCLUDING CROSS-LINKED MATERIAL

(71) Applicants: Samsung Electronics Co., Ltd., Suwon-si, Gyeonggi-do (KR); THE REGENTS OF THE UNIVERSITY OF MICHIGAN, Ann Arbor, MI (US)

(72) Inventors: Changho Noh, Suwon-si (KR); Min Sang Kwon, Ann Arbor, MI (US); Jinsang Kim, Ann Arbor, MI (US); Youngchang Yu, Ann Arbor, MI (US)

(73) Assignees: SAMSUNG ELECTRONICS CO., LTD., Gyeonggi-Do (KR); THE REGENTS OF THE UNIVERSITY OF MICHIGAN, An Arbor, MI (US)

( * ) Notice: Subject to any disclaimer, the term of this patent is extended or adjusted under 35 U.S.C. 154(b) by 119 days.

(21) Appl. No.: 15/176,646

(22) Filed: Jun. 8, 2016

(65) Prior Publication Data

US 2017/0162789 A1    Jun. 8, 2017

(30) Foreign Application Priority Data

Dec. 8, 2015    (KR) .................. 10-2015-0174155

(51) Int. Cl.
*H01L 51/00* (2006.01)
*C07C 47/575* (2006.01)
(Continued)

(52) U.S. Cl.
CPC .......... *H01L 51/004* (2013.01); *C07C 47/575* (2013.01); *C07D 207/452* (2013.01);
(Continued)

(58) Field of Classification Search
CPC ................ C08F 212/08; C08F 2220/301; C08F 212/14; C08F 2800/10; C08F 2500/26;
(Continued)

(56) References Cited

U.S. PATENT DOCUMENTS 8,525,131 B2    9/2013 Kim et al.
2012/0248337 A1    10/2012 Kim et al.

FOREIGN PATENT DOCUMENTS

JP    2007-112776 A    5/2007

OTHER PUBLICATIONS

Min Sang Kwon et al. "Suppressing molecular motions for enhanced room-temperature phosphorescence of metal-free organic materials", Nature Communications, 2015, 6:8947 DOI: 10.1038/ncomms9947, pp. 1-9.

(Continued)

*Primary Examiner* — Golam Mowla
(74) *Attorney, Agent, or Firm* — Cantor Colburn LLP

(57) ABSTRACT

A compound for an organic light-emitting device represented by Formula 1:

$$R_2-(L_1)_{n1}-\underset{\underset{X}{|}}{\overset{\overset{O}{\|}}{A_1}}\overset{R_1}{-}(L_2)_{n2}-R_3$$

Formula 1 wherein, in Formula 1,
$A_1$ is selected from an aromatic group and an aromatic group having extended π-conjugation,
$R_1$ is selected from hydrogen and a $C_1$-$C_{60}$ alkyl group, (Continued)

$L_1$ and $L_2$ are each independently selected from —O—, —S—, a $C_1$-$C_{20}$ alkylene group, a $C_1$-$C_{20}$ oxyalkylene group, and a $C_1$-$C_{20}$ thioalkylene group; and a $C_1$-$C_{20}$ alkylene group, a $C_1$-$C_{20}$ oxyalkylene group, and a $C_1$-$C_{20}$ thioalkylene group, each substituted with at least one selected from a $C_1$-$C_{20}$ alkyl group and a $C_1$-$C_{20}$ alkoxy group, n1 and n2 are each independently selected from 0, 1, 2, 3, 4, and 5, $R_2$ and $R_3$ are each independently selected from hydrogen and a first cross-linking group, provided that at least one of $R_2$ and $R_3$ is the first cross-linking group, and X is selected from —F, —Cl, —Br, and —I.

20 Claims, 8 Drawing Sheets

(51) Int. Cl.
| | |
|---|---|
| C07D 207/452 | (2006.01) |
| C08F 212/08 | (2006.01) |
| C08F 212/14 | (2006.01) |
| C08F 222/20 | (2006.01) |
| C08F 222/32 | (2006.01) |
| C08F 222/38 | (2006.01) |
| C08F 222/40 | (2006.01) |
| C08J 5/18 | (2006.01) |
| C09K 11/02 | (2006.01) |
| C09K 11/06 | (2006.01) |
| C08F 12/18 | (2006.01) |
| C09D 125/14 | (2006.01) |
| C09D 125/18 | (2006.01) |
| H01L 51/50 | (2006.01) |

(52) U.S. Cl.
CPC ............ *C08F 12/18* (2013.01); *C08F 212/08* (2013.01); *C08F 212/14* (2013.01); *C08F 222/20* (2013.01); *C08F 222/32* (2013.01); *C08F 222/38* (2013.01); *C08F 222/40* (2013.01); *C08J 5/18* (2013.01); *C09D 125/14* (2013.01); *C09D 125/18* (2013.01); *C09K 11/025* (2013.01); *C09K 11/06* (2013.01); *H01L 51/005* (2013.01); *H01L 51/0043* (2013.01); *H01L 51/0067* (2013.01); *C08F 2222/328* (2013.01); *C08F 2500/26* (2013.01); *C08F 2800/10* (2013.01); *C08J 2335/02* (2013.01); *C09K 2211/1007* (2013.01); *C09K 2211/1022* (2013.01); *C09K 2211/1029* (2013.01); *H01L 51/0008* (2013.01); *H01L 51/5012* (2013.01); *H01L 51/5016* (2013.01); *H01L 2251/5376* (2013.01)

(58) Field of Classification Search
CPC ............ C08F 2222/328; C08F 222/40; C08F 222/38; C08F 222/32; C08F 222/20; C08F 12/18; C07C 47/575; H01L 2251/5376; H01L 51/5012; H01L 51/0067; H01L 51/005; H01L 51/0043; H01L 51/004; H01L 51/0008; H01L 51/5016; C09K 2211/1029; C09K 2211/1022; C09K 2211/1007; C09K 11/06; C09K 11/025; C08J 2335/02; C08J 5/18; C09D 125/14; C09D 125/18

See application file for complete search history.

(56) References Cited

OTHER PUBLICATIONS

Min Sang Kwon et al. "Tailoring Intermolecular Interactions for Efficient Room-Temperature Phosphorescence from Purely Organic Materials in Amorphous Polymer Matrices", Angew. Chem. Int. Ed. 2014, 53, 11177-11181.

Onas Bolton et al. "Activating efficient phosphorescence from purely organic materials by crystal design", Nature Chemistry, vol. 3, Mar. 2011, pp. 205-210.

COMPOUND FOR ORGANIC LIGHT-EMITTING DEVICE, CROSS-LINKED MATERIAL THEREOF, AND ORGANIC LIGHT-EMITTING DEVICE INCLUDING CROSS-LINKED MATERIAL

STATEMENT OF FEDERAL FUNDING

This invention was made with government support under Grant No. DMR1435965 awarded by the National Science Foundation. The government has certain rights in the invention.

CROSS-REFERENCE TO RELATED APPLICATION

This application claims priority to and the benefit of Korean Patent Application No. 10-2015-0174155, filed on Dec. 8, 2015, in the Korean Intellectual Property Office, the content of which is incorporated herein in its entirety by reference.

BACKGROUND

1. Field

The present disclosure relates to a compound for an organic light-emitting device, a cross-linked material thereof, and an organic light-emitting device including the cross-linked material.

2. Description of the Related Art

Organic light-emitting devices (OLEDs) are self-emission devices that have wide viewing angles, high contrast ratios, and short response times. In addition, the OLEDs exhibit high luminance, driving voltage, and response speed characteristics, and produce full-color images.

Typical OLEDs include an anode, a cathode, and an organic layer that is between the anode and the cathode and includes an emission layer. A hole transport region may be disposed between the anode and the emission layer, and an electron transport region may be between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons change from an excited state to a ground state to thereby generate light.

Various types of organic light emitting devices are known. However, there still remains a need in OLEDs having low driving voltage, high efficiency, high brightness, and long lifespan.

SUMMARY

Provided is a compound for an organic light-emitting device, a cross-linked material thereof, and an organic light-emitting device including the cross-linked material.

Additional aspects will be set forth in part in the description which follows and, in part, will be apparent from the description, or may be learned by practice of the presented embodiments.

According to an aspect of an embodiment, a compound for an organic light-emitting device is represented by Formula 1:

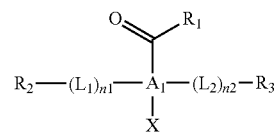

Formula 1 wherein, in Formula 1, $A_1$ is selected from an aromatic group and an aromatic group having extended π-conjugation, $R_1$ is selected from hydrogen and a $C_1$-$C_{60}$ alkyl group, $L_1$ and $L_2$ are each independently selected from —O—, —S—, a $C_1$-$C_{20}$ alkylene group, a $C_1$-$C_{20}$ oxyalkylene group, and a $C_1$-$C_{20}$ thioalkylene group; and a $C_1$-$C_{20}$ alkylene group, a $C_1$-$C_{20}$ oxyalkylene group, and a $C_1$-$C_{20}$ thioalkylene group, each substituted with at least one selected from a $C_1$-$C_{20}$ alkyl group and a $C_1$-$C_{20}$ alkoxy group, n1 and n2 are each independently selected from 0, 1, 2, 3, 4, and 5, $R_2$ and $R_3$ are each independently selected from hydrogen and a first cross-linking group, provided that at least one of $R_2$ and $R_3$ is the first cross-linking group, X is selected from —F, —Cl, —Br, and —I.

According to an aspect of another embodiment, a cross-linked material of a compound for an organic light-emitting device represented by Formula 1 and a polymer is provided.

According to an aspect of still another embodiment, an organic light-emitting device may include:

a first electrode;

a second electrode; and an organic layer disposed between the first electrode and the second electrode, wherein the organic layer includes an emission layer and at least one cross-linked material.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
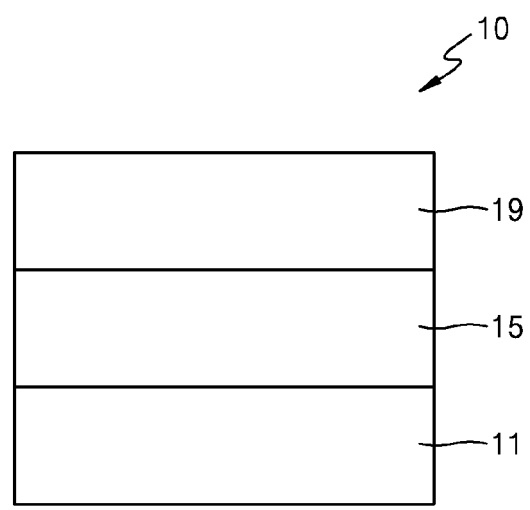
FIG. 1 is a schematic cross-sectional view illustrating an organic light-emitting device according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

A compound for an organic light-emitting device may be represented by Formula 1 and include at least one first cross-linking group:

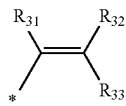

Formula 1

When the compound for an organic light-emitting device represented by Formula 1 includes at least two first cross-linking groups, the first cross-linking groups may be identical to or different from each other.

In some embodiments, in Formula 1, the first cross-linking group may include at least one carbon-carbon double bond.

In some embodiments, in Formula 1, the first cross-linking group may include a substructure represented by one of Formulae 3-1 and 3-2, but embodiments are not limited thereto:

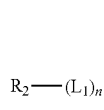

3-1

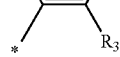

3-2

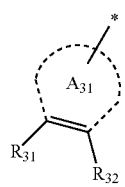

wherein, in Formulae 3-1 and 3-2, $A_{31}$ may be selected from a $C_5$-$C_{10}$ cyclic group and a $C_1$-$C_{10}$ heterocyclic group; and a $C_5$-$C_{10}$ cyclic group and a $C_1$-$C_{10}$ heterocyclic group, each substituted with at least one selected from —F, —Cl, —Br, —I, —C(=O)—, a cyano group, a nitro group, a $C_1$-$C_{20}$ alkyl group, and a $C_1$-$C_{20}$ alkoxy group, $R_{31}$ to $R_{33}$ may be each independently selected from hydrogen, —F, —Cl, —Br, —I, —C(=O)—, a cyano group, a nitro group, a $C_1$-$C_{20}$ alkyl group, and a $C_1$-$C_{20}$ alkoxy group, and

* indicates a binding site to an adjacent atom.

In some embodiments, in Formula 1, the first cross-linking group may be selected from a vinyl group, a maleimide group, a styrene group, and an acrylate group; and a vinyl group, a maleimide group, a styrene group, and an acrylate group, each substituted with at least one selected from —F, —Cl, —Br, —I, —C(=O)—, a cyano group, a nitro group, a $C_1$-$C_{20}$ alkyl group, and a $C_1$-$C_{20}$ alkoxy group, but embodiments are not limited thereto.

In some embodiments, in Formula 1, the first cross-linking group may be selected from groups represented by Formulae 3-11 to 3-14, but embodiments are not limited thereto:

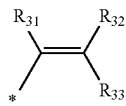

3-11

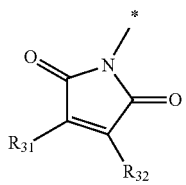

3-12

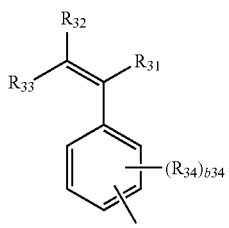

3-13

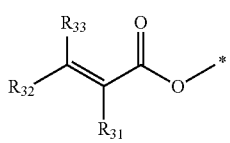

3-14 wherein, in Formulae 3-11 to 3-14, $R_{31}$ to $R_{34}$ may be each independently selected from hydrogen, —F, —Cl, —Br, —I, —C(=O)—, a cyano group, a nitro group, a $C_1$-$C_{20}$ alkyl group, and a $C_1$-$C_{20}$ alkoxy group, and

* indicates a binding site to an adjacent atom.

In some embodiments, in Formulae 3-11 to 3-14, $R_{31}$ to $R_{34}$ may be each independently selected from hydrogen, a methyl group, an ethyl group, an n-propyl group, an iso-propyl group, a methoxy group, an ethoxy group, an n-propoxy group, and an iso-propoxy group, but embodiments are not limited thereto.

In some embodiments, in Formulae 3-11 to 3-14, $R_{31}$ to $R_{34}$ may each be hydrogen, but embodiments are not limited thereto.

In Formula 1, $A_1$ may be selected from an aromatic group and an aromatic group having extended π-conjugation.

In some embodiments, in Formula 1, $A_1$ may be selected from a phenyl group and a naphthyl group, but embodiments are not limited thereto.

In Formula 1, $R_1$ may be selected from hydrogen and a $C_1$-$C_{60}$ alkyl group, but embodiments are not limited thereto.

In some embodiments, in Formula 1, $R_1$ may be hydrogen, but embodiments are not limited thereto.

In Formula 1, $L_1$ and $L_2$ may be each independently selected from —O—, —S—, a $C_1$-$C_{20}$ alkylene group, a $C_1$-$C_{20}$ oxyalkylene group, and a $C_1$-$C_{20}$ thioalkylene group; and a $C_1$-$C_{20}$ alkylene group, a $C_1$-$C_{20}$ oxyalkylene group, and a $C_1$-$C_{20}$ thioalkylene group, each substituted with at least one selected from a $C_1$-$C_{20}$ alkyl group and a $C_1$-$C_{20}$ alkoxy group.

In some embodiments, in Formula 1, $L_1$ and $L_2$ may be each independently selected from —O— and a $C_1$-$C_{20}$ alkylene group, but embodiments are not limited thereto.

In some embodiments, in Formula 1, $L_1$ and $L_2$ may be each independently selected from —O—, a methylene group, an ethylene group, and a propylene group, but embodiments are not limited thereto.

In Formula 1, n1 indicates the number of groups $L_1$, and n1 may be selected from 0, 1, 2, 3, 4, and 5. When n1 is 0, $(L_1)_{n1}$ may be a single bond. When n1 is 2 or more, groups $L_1$ may be identical to or different from each other. In some embodiments, in Formula 1, n1 may be selected from 0, 1, and 2.

In Formula 1, n2 indicates the number of groups $L_2$, and n2 may be selected from 0, 1, 2, 3, 4, and 5. When n2 is 0, $(L_2)_{n2}$ may be a single bond. When n2 is 2 or more, groups $L_2$ may be identical to or different from each other. In some embodiments, in Formula 1, n2 may be selected from 0, 1, and 2.

In Formula 1, $R_2$ and $R_3$ may be each independently selected from hydrogen and a first cross-linking group, provided that at least one of $R_2$ and $R_3$ may be the first cross-linking group.

In some embodiments, in Formula 1, $R_2$ and $R_3$ may be each independently selected from hydrogen and groups represented by Formulae 3-11 to 3-14.

At least one of $R_2$ and $R_3$ may be selected from groups represented by Formulae 3-11 to 3-14, but embodiments are not limited thereto:

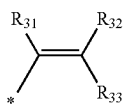

3-11

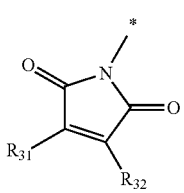

3-12

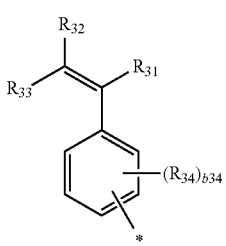

3-13

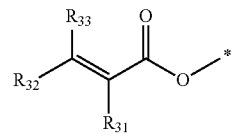

3-14 wherein, in Formulae 3-11 to 3-14, $R_{31}$ to $R_{34}$ may be each independently selected from hydrogen, —F, —Cl, —Br, —I, —C(=O)—, a cyano group, a nitro group, a $C_1$-$C_{20}$ alkyl group, and a $C_1$-$C_{20}$ alkoxy group, and b34 may be selected from 1, 2, 3, and 4, and

* indicates a binding site to an adjacent atom.

In some embodiments, in Formula 1, $R_2$ and $R_3$ may be a first cross-linking group, but embodiments are not limited thereto.

In Formula 1, X may be selected from —F, —Cl, —Br, and —I.

In some embodiments, in Formula 1, X may be —Br.

In some embodiments, the compound for an organic light-emitting device represented by Formula 1 may be Compound DA1, but embodiments are not limited thereto:

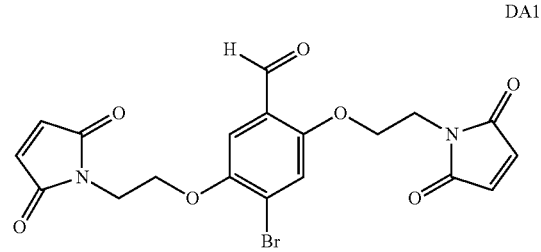 [SMILES: O=Cc1cc(OCCN2C(=O)C=CC2=O)c(Br)cc1OCCN1C(=O)C=CC1=O]

DA1

In general, metal-free phosphorescent materials are less efficient in spin-orbit coupling (SOC), and SOC competes with non-radiative decay. Phosphorescence process is significantly slow, as compared with non-radiative decay. Therefore, in order for an organic phosphor to exhibit high phosphorescence quantum efficiency, non-radiative decay may essentially be suppressed.

The compound for an organic light-emitting device represented by Formula 1 includes bromine and benzaldehyde, promoting intersystem crossing (ISC) via SOC by the creation of an nπ*-type triplet ($T_n$) state, due to the intramolecular and intermolecular heavy atom effect of bromine and benzaldehyde and ISC promoting effect by the El-Sayed rule.

A method of synthesizing the compound for an organic light-emitting device represented by Formula 1 may be understood by one of ordinary skill in the art by referring to Synthesis Examples described below.

According to another aspect, a cross-linked material of a compound for an organic light-emitting device represented by Formula 1 and a polymer is provided.

In some embodiments, the cross-linked material may include a constituent unit represented by one of Formulae 2-1 to 2-3:

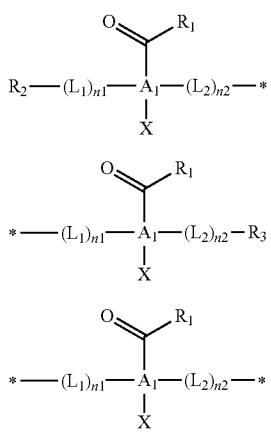

Formula 2-1

Formula 2-2

Formula 2-3 wherein, in Formulae 2-1 to 2-3, $A_1$ may be selected from an aromatic group and an aromatic group having extended π-conjugation, $R_1$ may be selected from hydrogen and a $C_1$-$C_{60}$ alkyl group, $L_1$ and $L_2$ may be each independently selected from —O—, —S—, a $C_1$-$C_{20}$ alkylene group, a $C_1$-$C_{23}$ oxyalkylene group, and a $C_1$-$C_{23}$ thioalkylene group, n1 and n2 may be each independently selected from 0, 1, 2, 3, 4, and 5, $R_2$ and $R_3$ may be each independently selected from hydrogen and a first cross-linking group, provided that at least one of $R_2$ and $R_3$ may be the first cross-linking group, X may be selected from —F, —Cl, —Br, and —I, and

* indicates a binding site to an adjacent atom.

The polymer may be a homopolymer or a copolymer. When the polymer is a copolymer, the binding method is not particularly limited. In some embodiments, the polymer in the compound for an organic light-emitting device may be one selected from a random copolymer, an alternating copolymer, a periodic copolymer, and a block copolymer, but embodiments are not limited thereto.

In some embodiments, the polymer may be a vinyl polymer, but embodiments are not limited thereto.

In some embodiments, the polymer may be a vinyl polymer and include a small pendant, but embodiments are not limited thereto.

In some embodiments, the polymer may include a repeating unit (1) represented by Formula 4, and the repeating unit (1) may include at least one second cross-linking group:

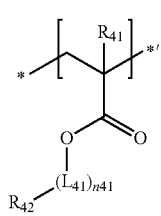

Formula 4 wherein, in Formula 4, $L_{41}$ may be selected from —O—, —S—, a $C_1$-$C_{20}$ alkylene group, a $C_1$-$C_{20}$ oxyalkylene group, and a $C_1$-$C_{20}$ thioalkylene group; and a $C_1$-$C_{20}$ alkylene group, a $C_1$-$C_{23}$ oxyalkylene group, and a $C_1$-$C_{20}$ thioalkylene group, each substituted with at least one selected from a $C_1$-$C_{20}$ alkyl group and a $C_1$-$C_{20}$ alkoxy group, n41 may be selected from 0, 1, 2, 3, 4, and 5, $R_{41}$ may be selected from hydrogen, a $C_1$-$C_{20}$ alkyl group, and a $C_1$-$C_{20}$ alkoxy group, $R_{42}$ may be a second cross-linking group, and

* and *' each indicate a binding site to an adjacent atom.

When the polymer including the repeating unit (1) represented by Formula 4 includes a plurality of second cross-linking groups, the second cross-linking groups may be identical to or different from each other.

In some embodiments, in Formula 4, the second cross-linking group may include at least two double bonds selected from a carbon-carbon double bond and a carbon-oxygen double bond.

In some embodiments, in Formula 4, the second cross-linking group may be selected from a 1,3-butadienyl group and a furanyl group; and a 1,3-butadienyl group and a furanyl group, each substituted with at least one selected from —F, —Cl, —Br, —I, —C(=O)—, a cyano group, a nitro group, a $C_1$-$C_{20}$ alkyl group, and a $C_1$-$C_{20}$ alkoxy group, but embodiments are not limited thereto.

In some embodiments, in Formula 4, the second cross-linking group may be represented by Formula 5, but embodiments are not limited thereto:

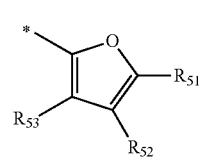

Formula 5 wherein, in Formula 5, $R_{51}$ to $R_{53}$ may be each independently selected from hydrogen, —F, —Cl, —Br, —I, —C(=O)—, a cyano group, a nitro group, a $C_1$-$C_{20}$ alkyl group, and a $C_1$-$C_{20}$ alkoxy group, and

* indicates a binding site to an adjacent atom.

In some embodiments, in Formula 5, $R_{51}$ to $R_{53}$ may be each independently selected from hydrogen, —F, —Cl, —Br, —I, —C(=O)—, a cyano group, and a nitro group, but embodiments are not limited thereto.

In some embodiments, in Formula 4, $R_{41}$ may be selected from hydrogen and a methyl group, but embodiments are not limited thereto.

In some embodiments, the polymer may include a repeating unit (1) represented by Formula 4-1, but embodiments are not limited thereto:

Formula 4-1

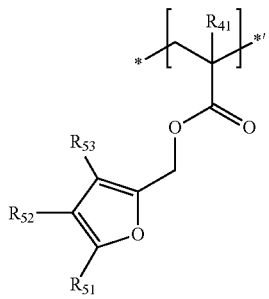

wherein, in Formula 4-1, $R_{41}$ may be selected from hydrogen and a methyl group, $R_{51}$ to $R_{53}$ may be each independently selected from hydrogen, —F, —Cl, —Br, —I, —C(=O)—, a cyano group, and a nitro group, and

* and *' each indicate a binding site to an adjacent atom.

In some embodiments, the polymer may include a repeating unit (1) selected from repeating units represented by Formulae 4-11 and 4-12, but embodiments are not limited thereto:

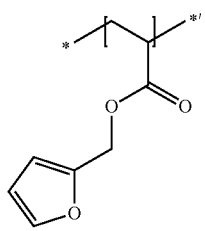
4-11

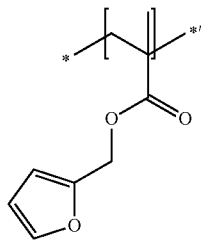
4-12 wherein, in Formulae 4-11 and 4-12,

* and *' each indicate a binding site to an adjacent atom.

In some embodiments, the polymer may include the repeating unit (1) as well as a repeating unit (2) selected from repeating units represented by Formulae 6-1 to 6-4, but embodiments are not limited thereto:

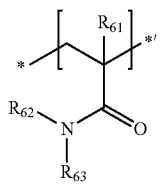
6-1

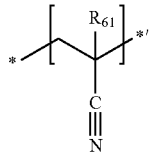
6-2

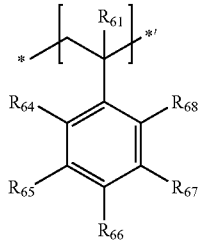
6-3

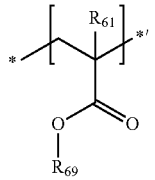
6-4 wherein, in Formulae 6-1 to 6-4, $R_{61}$ may be selected from hydrogen, a $C_1$-$C_{20}$ alkyl group, and a $C_1$-$C_{20}$ alkoxy group, $R_{62}$ to $R_{69}$ may be each independently selected from hydrogen, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from —F, —Cl, —Br, —C(=O)—, a cyano group, and a nitro group, $R_{62}$ and $R_{63}$ may optionally be bound to each other to form a ring, and

* and *' each indicate a binding site to an adjacent atom.

In some embodiments, the polymer may include the repeating unit (1) as well as a repeating unit (2) selected from repeating units represented by Formulae 6-11 to 6-16, but embodiments are not limited thereto:

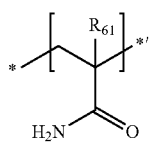
6-11

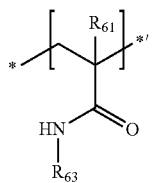
6-12

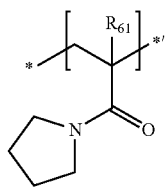
6-13

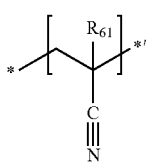
6-14

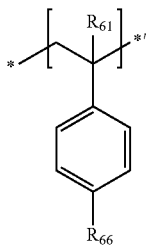
6-15

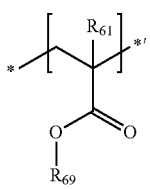
6-16 wherein, in Formulae 6-11 to 6-16, $R_{61}$ may be selected from hydrogen and a methyl group, $R_{63}$, $R_{66}$, and $R_{69}$ may be each independently selected from a methyl group, an ethyl group, an n-propyl group, and an iso-propyl group;

a methyl group, an ethyl group, an n-propyl group, and an iso-propyl group, each substituted with at least one selected from —F, —Cl, —Br, —I, —C(=O)—, a cyano group, and a nitro group, and

* and *' each indicate a binding site to an adjacent atom.

In some embodiments, the polymer may include the repeating unit (1) as well as a repeating unit (2) selected from repeating units represented by Formulae 6-21 to 6-34, but embodiments are not limited thereto:

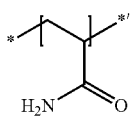
6-21

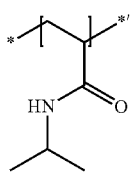
6-22

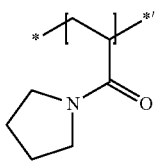
6-23

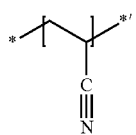
6-24

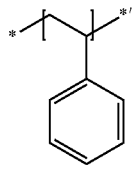
6-25

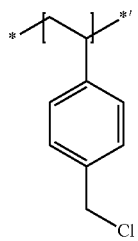
6-26

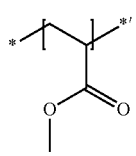
6-27

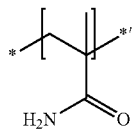
6-28

6-29

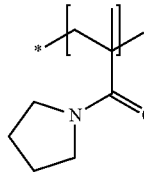
6-30

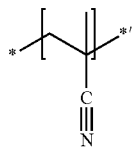
6-31

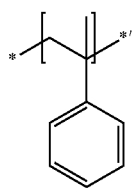
6-32

-continued

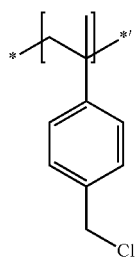

6-33

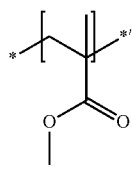

6-34

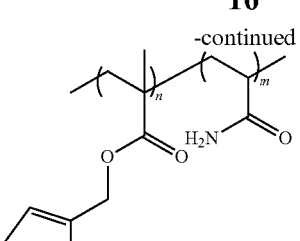

P(FMA-r-AM)

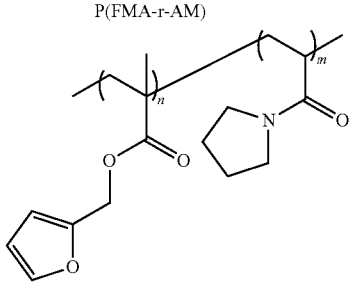

P(FMA-r-AP)

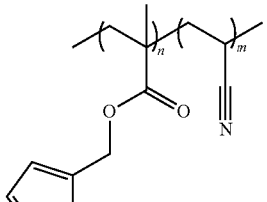

P(FMA-r-AN)

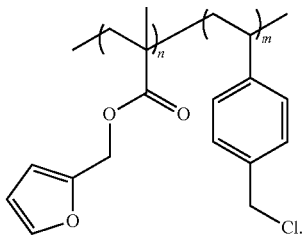

P(FMA-r-VBC)

wherein, in Formulae 6-21 and 6-34,

* and *' each indicate a binding site to an adjacent atom.

In some embodiments, the polymer may include the repeating unit (1) represented by one of Formulae 4-11 and 4-12 as well as a repeating unit (2) selected from repeating units represented by Formulae 6-21 to 6-34, but embodiments are not limited thereto.

In some embodiments, the polymer may be selected from poly(furfuryl methacrylate) (PFMA) homopolymer, poly (furfuryl methacrylate-r-methyl methacrylate) random copolymer (P(FMA-r-MMA)), poly(furfuryl methacrylate-r-N-isopropylacrylamide) random copolymer (P(FMA-r-NiPAM)), poly(furfuryl methacrylate-r-styrene) random copolymer (P(FMA-r-S)), poly(furfuryl methacrylate-r-acrylamide) random copolymer (P(FMA-r-AM)), poly(furfuryl methacrylate-r-acrylpyrrolidine) random copolymer (P(FMA-r-AP)), poly(furfuryl methacrylate-r-acetonitrile) random copolymer (P(FMA-r-AN)), and poly(furfuryl methacrylate-r-vinylbenzyl chloride) random copolymer (P(FMA-r-VBC)), but embodiments are not limited thereto:

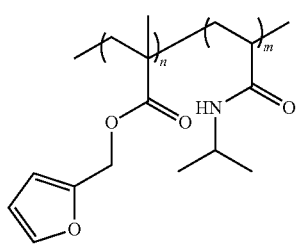

P(FMA-r-NiPAM)

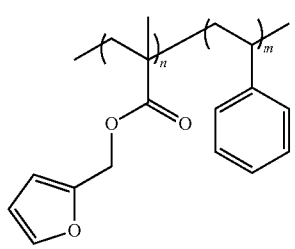

P(FMA-r-S)

The compound for an organic light-emitting device represented by Formula 1 may be bound to a polymer via a covalent linkage, thus forming the cross-linked material. The covalent linkage, may be, for example, formed through a Diels-Alder reaction, but embodiments are not limited thereto.

The covalent linkage may restrict the molecular motions in the proximity of the compound (which may serve as a fluorescent substance) for an organic light-emitting device represented by Formula 1 embedded in a polymer matrix and hence effectively suppress the non-radiative decay. In particular, the covalent linkage may reduce: i) the collision frequency (endothermic triplet-triplet energy transfer process) and ii) vibronic mixing between zero-order electronic states of $T_1$ and $S_0$ that directs the reduction of the rate of the ISG process. Therefore, the cross-linked material of a compound for an organic light-emitting device represented by Formula 1 and a polymer may significantly increase phosphorescence quantum yield, and an organic light-emitting device including cross-linked material may have high efficiency.

Therefore, the phosphorescence quantum yield of the cross-linked material may be 2 to 5 times higher than that of a system having no such covalent linkage between the fluorescent substance and the polymer matrix.

A method of synthesizing the cross-linked material of a compound for an organic light-emitting device represented by Formula 1 and a polymer may be understood by one of ordinary skill in the art by referring to Synthesis Examples described below.

According to another aspect, an organic light-emitting device may include:
- a first electrode;
- a second electrode; and
- an organic layer disposed between the first electrode and the second electrode,
- wherein the organic layer includes an emission layer and the above-described cross-linked material.

The organic light-emitting device may include the above-described cross-linked material, thus exhibiting high efficiency.

In some embodiments, the emission layer may include the cross-linked material of a compound for an organic light-emitting device represented by Formula 1 and a polymer.

In some embodiments, the emission layer may include the cross-linked material of a compound for an organic light-emitting device represented by Formula 1 and a polymer, and the cross-linked material may be a phosphorescent material.

The emission layer may emit red light, green light, or blue light.

The first electrode may be anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example, the first electrode may be an anode, the second electrode may be a cathode, and the organic layer may include:
i) a hole transport region disposed between the first electrode and the emission layer, wherein the hole transport region may include at least one selected from a hole injection layer, a hole transport layer, and an electron blocking layer; and
ii) an electron transport region disposed between the emission layer and the second electrode, wherein the electron transport region may include at least one selected from a hole blocking layer, an electron transport layer, and an electron injection layer.

The term "organic layer" as used herein refers to a single and/or a plurality of layers disposed between the first electrode and the second electrode in an organic light-emitting device. The "organic layer" may include not only organic compounds but also organometallic complexes including metals.

FIG. 1 is a schematic view of an organic light-emitting device 10 according to an exemplary embodiment. Hereinafter a structure and a method of manufacturing the organic light-emitting device 10, according to an embodiment, will be described with reference to FIG. 1. The organic light-emitting device 10 may include a first electrode 11, an organic layer 15, and a second electrode 19, which may be sequentially layered in the stated order.

A substrate may be additionally disposed under the first electrode 11 or on the second electrode 19. The substrate may be a conventional substrate that is used in an organic light-emitting device, such as glass substrate or a transparent plastic substrate, each having excellent mechanical strength, thermal stability, transparency, surface smoothness, ease of handling, and water repellency.

The first electrode 11 may be formed by vacuum depositing or sputtering a material for forming the first electrode 11 on the substrate. The first electrode 11 may be an anode. The material for the first electrode 11 may be selected from materials with a high work function for easy hole injection. The first electrode 11 may be a reflective electrode, a semi-transmissive electrode, or a transmissive electrode. The material for the first electrode 11 may be selected from indium tin oxide (ITO), indium zinc oxide (IZO), tin oxide ($SnO_2$), and zinc oxide (ZnO). Alternatively, the material for the first electrode 11 may be a metal, such as magnesium (Mg), aluminum (Al), aluminum-lithium (Al—Li), calcium (Ca), magnesium-indium (Mg—In), and magnesium-silver (Mg—Ag).

The first electrode 11 may have a single layer structure or a multi-layer structure including a plurality of layers. In some embodiments, the first electrode 11 may have a triple-layer structure of ITO/Ag/ITO, but embodiments are not limited thereto.

The organic layer 15 may be on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include a hole injection layer only or a hole transport layer only. In some embodiments, the hole transport region may include a hole injection layer and a hole transport layer which are sequentially stacked on the first electrode 11. In some embodiments, the hole transport region may include a hole injection layer, a hole transport layer, and an electron blocking layer, which are sequentially stacked on the first electrode 11.

When the hole transport region includes a hole injection layer, the hole injection layer may be formed on the first electrode 11 by using a suitable method, such as vacuum deposition, spin coating, casting, and a Langmuir-Blodgett (LB) method.

When a hole injection layer is formed by vacuum-deposition, for example, the vacuum-deposition may be performed at a deposition temperature in a range of about 100° C. to about 500° C., at a vacuum degree in a range of about $10^{-8}$ to about $10^{-3}$ torr, and at a deposition rate in a range of about 0.01 Angstroms per second (Å/sec) to about 100 Å/sec, though the conditions may vary depending on a compound that is used as a hole injection material and a structure and thermal properties of a desired hole injection layer, but embodiments are not limited thereto.

When a hole injection layer is formed by spin coating, the spin coating may be performed at a coating rate in a range of about 2,000 revolutions per minute (rpm) to about 5,000 rpm, and at a temperature in a range of about 80° C. to 200° C. for removing a solvent after the spin coating, though the conditions may vary depending on a compound that is used as a hole injection material and a structure and thermal properties of a desired hole injection layer, but is not limited thereto.

The conditions for forming a hole transport layer and an electron blocking layer may be inferred based on the conditions for forming the hole injection layer.

The hole transport region may include at least one selected from m-MTDATA, TDATA, 2-TNATA, NPB, β-NPB, TPD, spiro-TPD, spiro-NPB, methylated-NPB, TAPC, HMTPD, 4,4',4''-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201, and a compound represented by Formula 202:

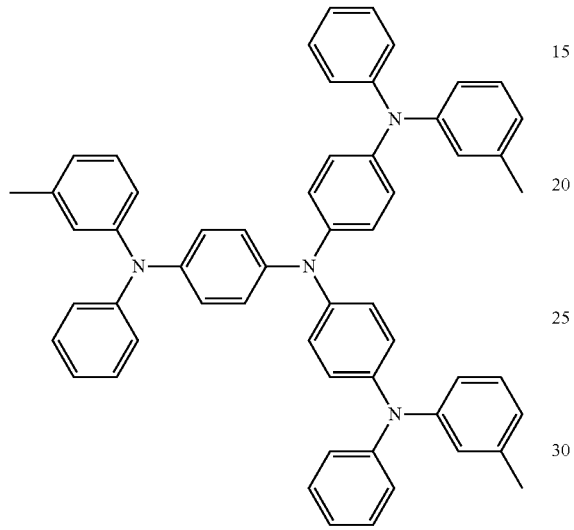

m-MTDATA

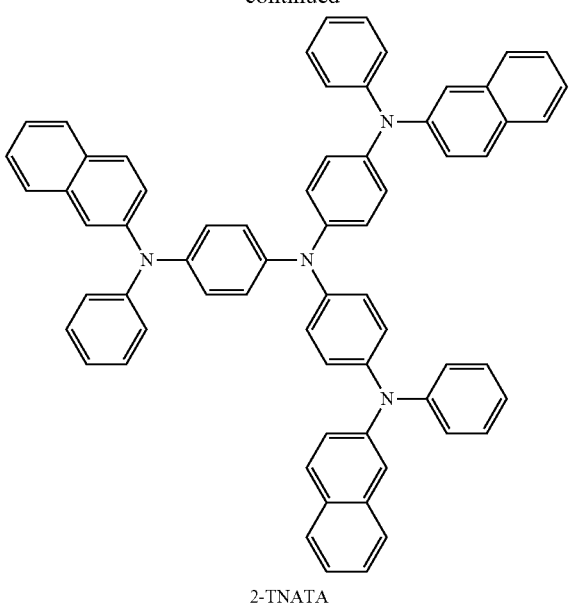

2-TNATA

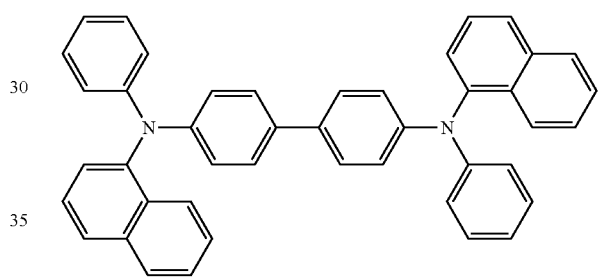

NPB

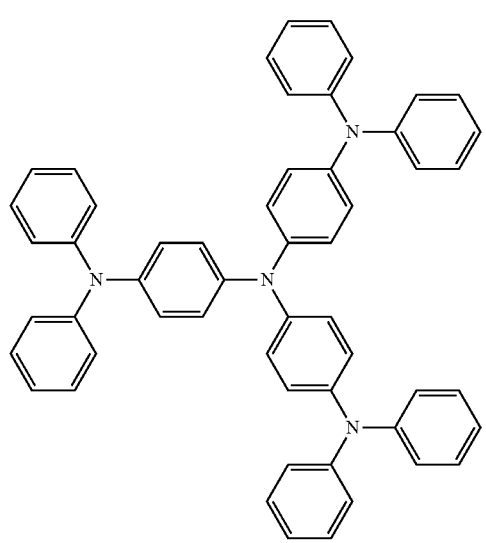

TDATA

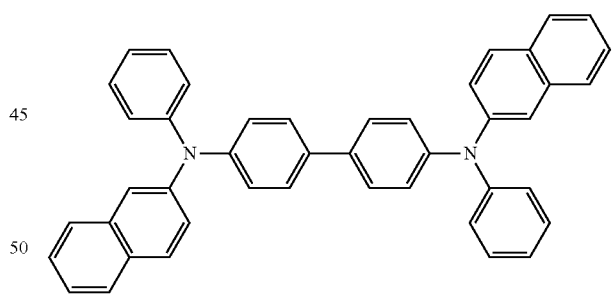

β-NPB

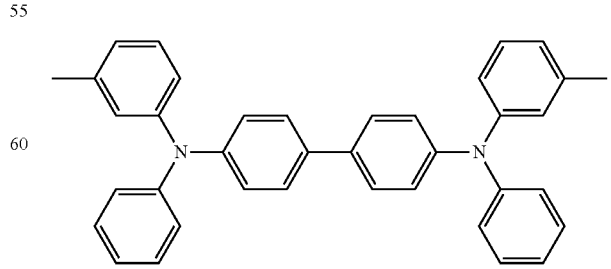

TPD

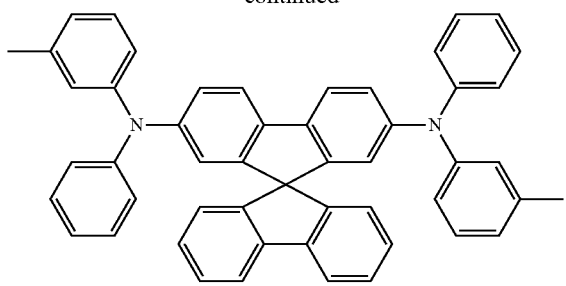

Spiro-TPD

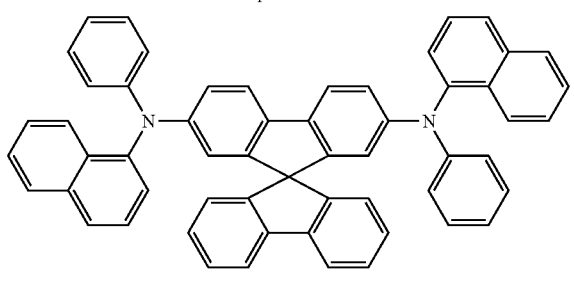

Spiro-NPB

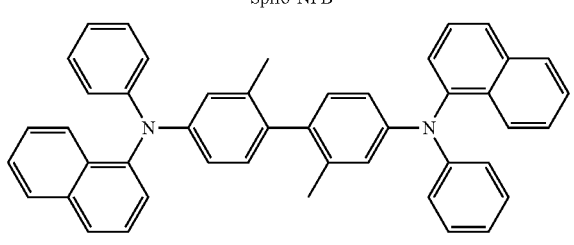

methylated NPB

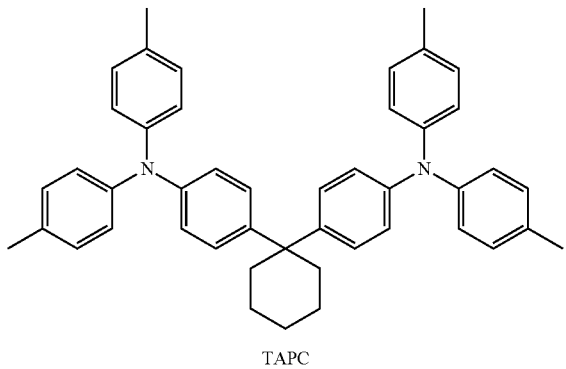

TAPC

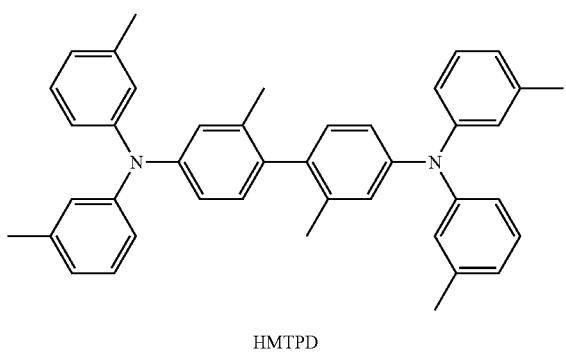

HMTPD

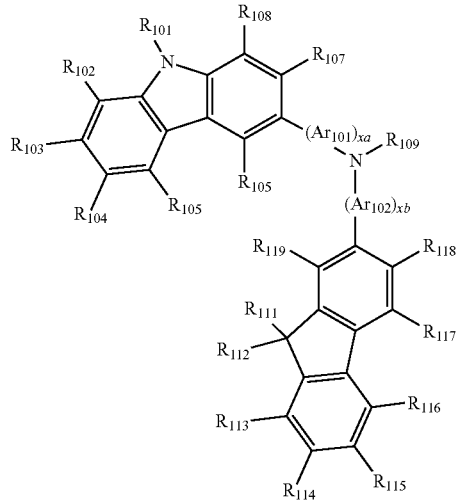

Formula 201

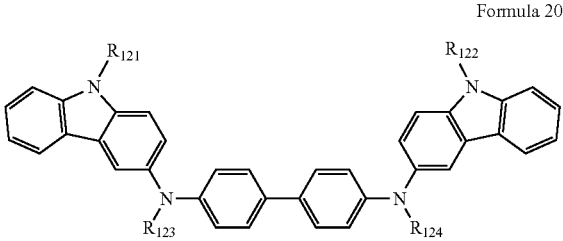

Formula 202 wherein, in Formula 201, $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

In Formula 201, xa and xb may be each independently an integer selected from 0 to 5. Alternatively, xa and xb may be each independently an integer selected from 0, 1, and 2. In some embodiments, xa may be 1 and xb may be 0, but embodiments are not limited thereto.

In Formulae 201 and 202, $R_{101}$ to $R_{108}$, $R_{111}$ to $R_{119}$, and $R_{121}$ to $R_{124}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, a pentyl group, or a hexyl group) and a $C_1$-$C_{10}$ alkoxy group (e.g., a methoxy group, an ethoxy group, a propoxy group, a butoxy group, or a pentoxy group);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

In Formula 201, $R_{109}$ may be selected from a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In some embodiments, the compound represented by Formula 201 may be represented by Formula 201A, but embodiments are not limited thereto:

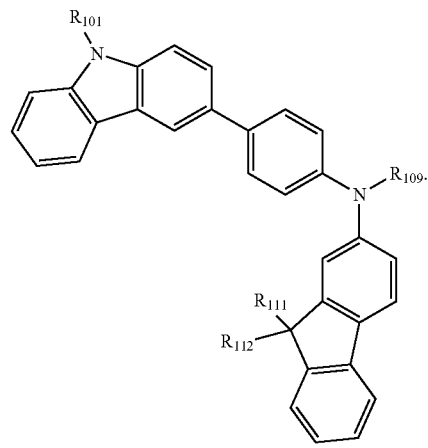

Formula 201A $R_{101}$, $R_{111}$, $R_{112}$, and $R_{109}$ in Formula 201 A may be the same as described herein.

For example, the compound represented by Formula 201 and the compound represented by Formula 202 may include Compounds HT1 to HT20, but embodiments are not limited thereto:

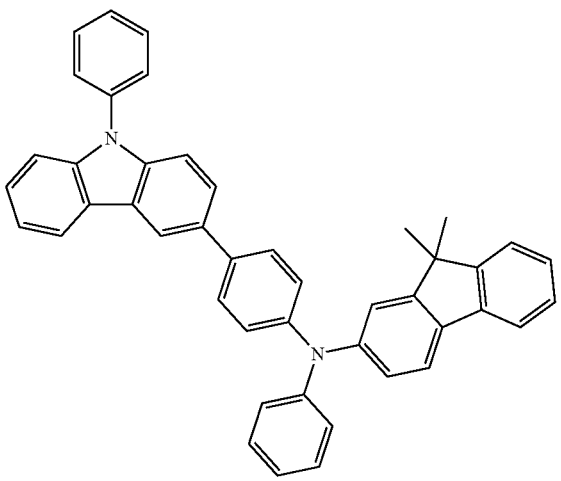

HT1

HT2
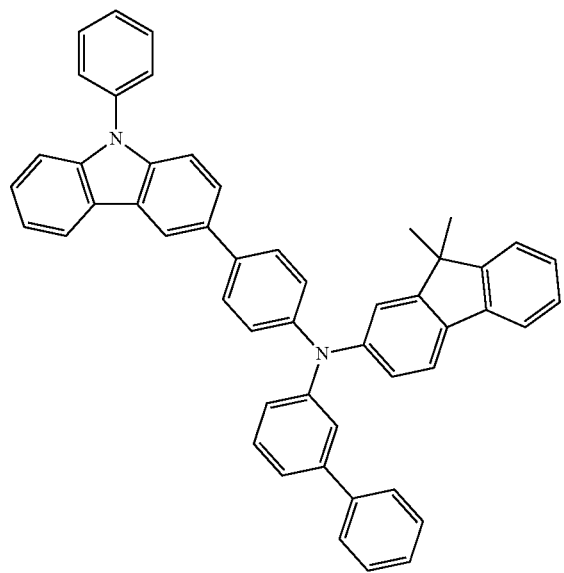
HT4
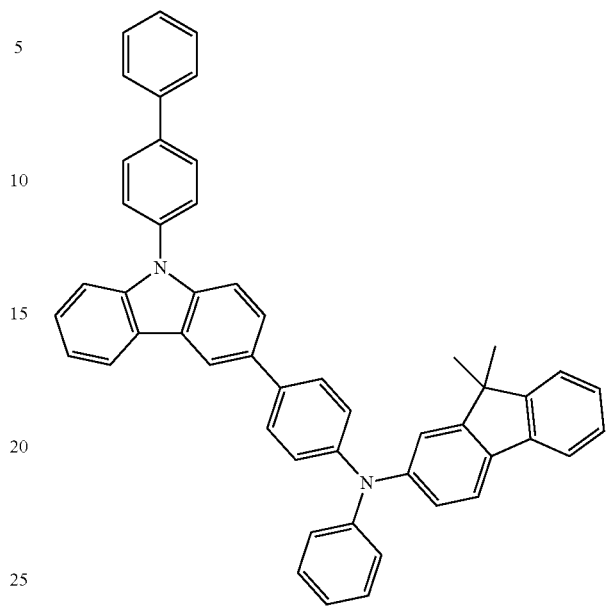
HT3
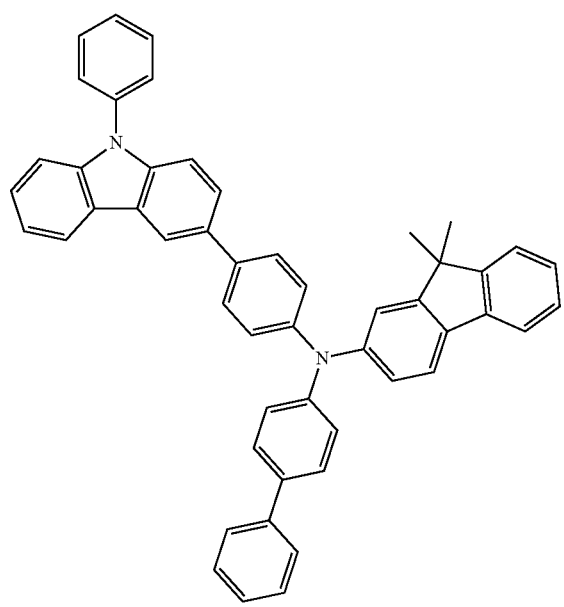
HT5
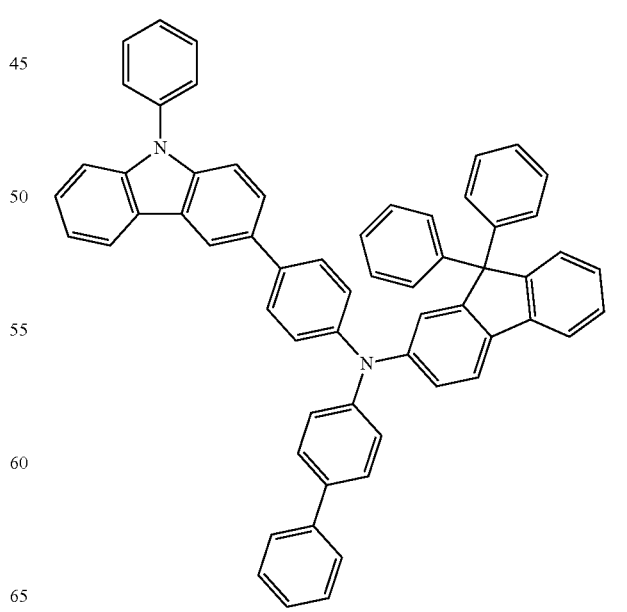

HT6
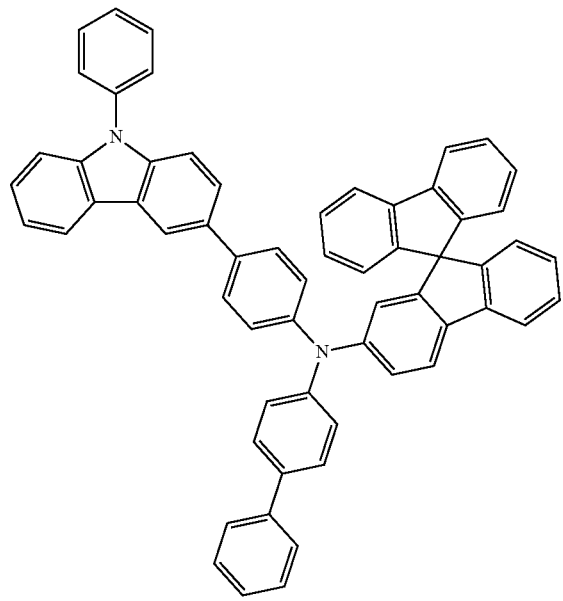
HT8
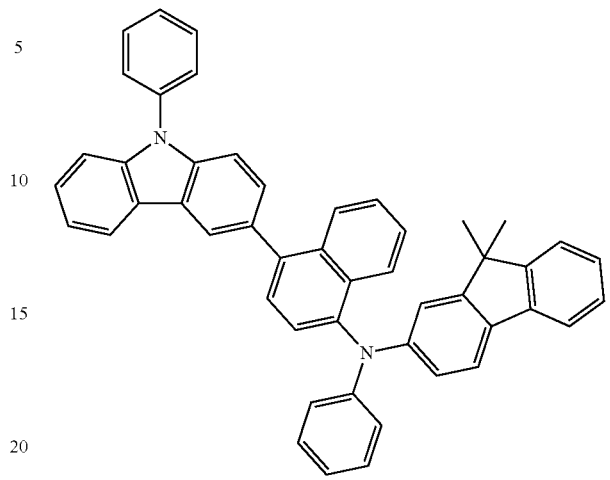
HT9
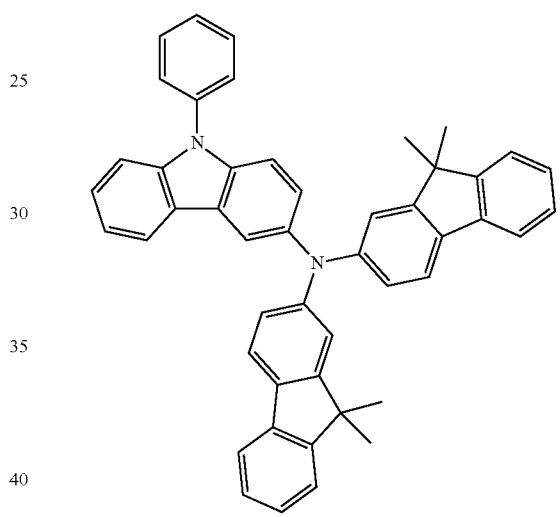
HT7
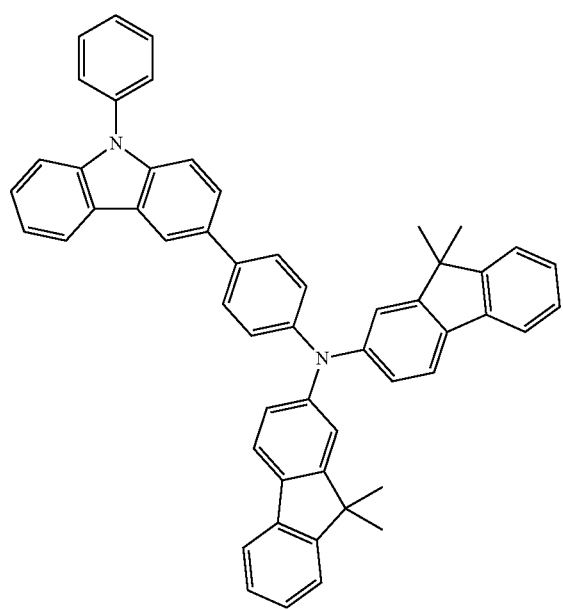
HT10
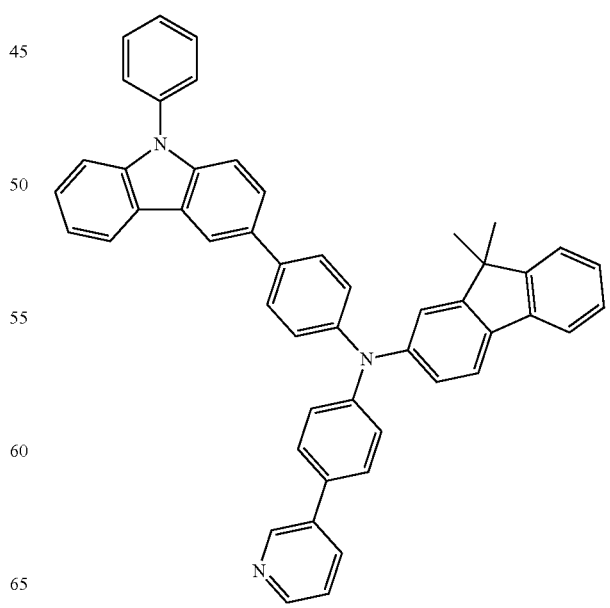

-continued
HT11
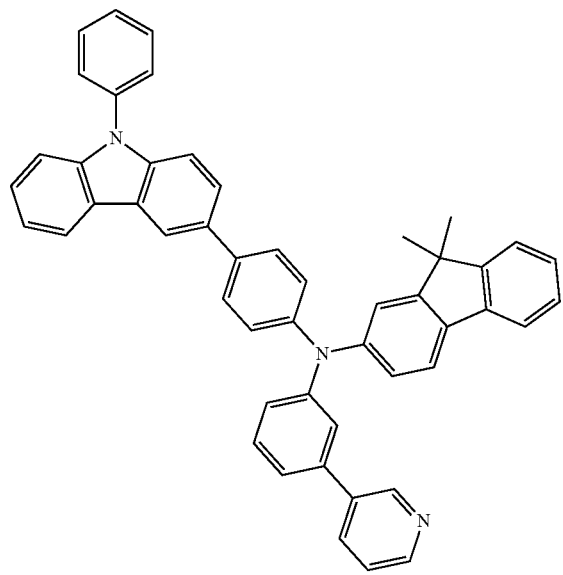
HT12
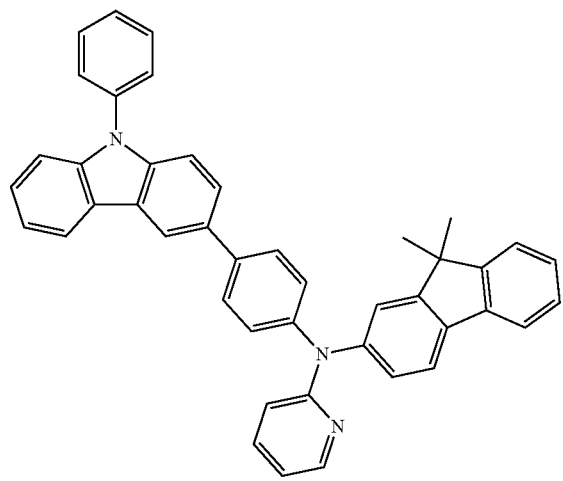
HT13
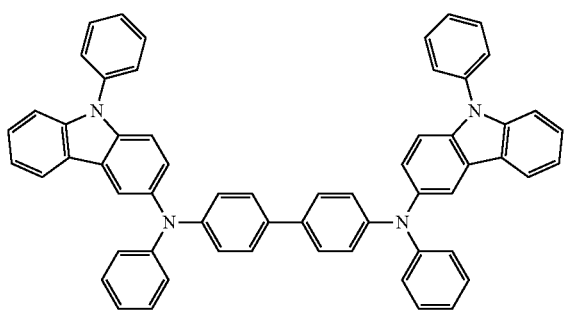
-continued
HT14
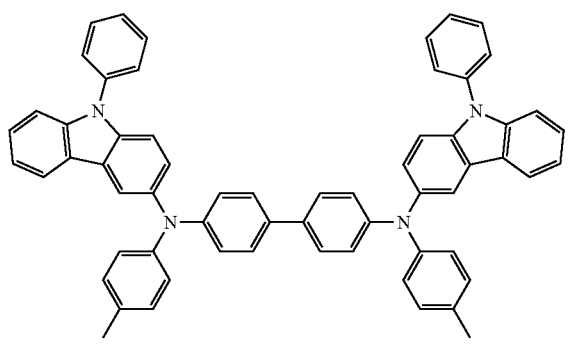
HT15
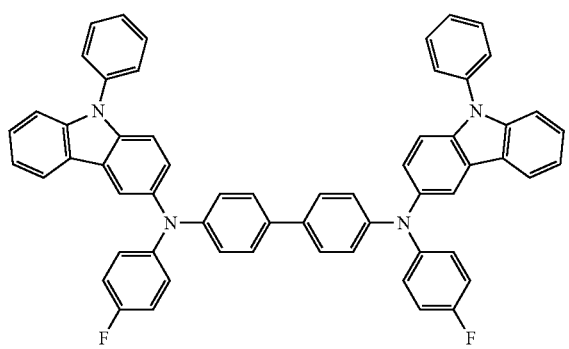
HT16
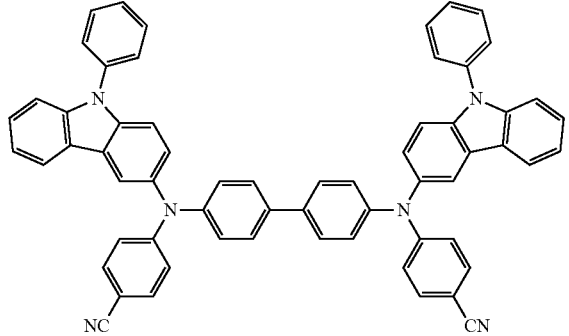
HT17
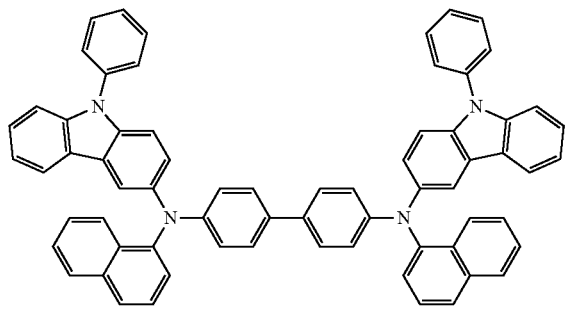

-continued

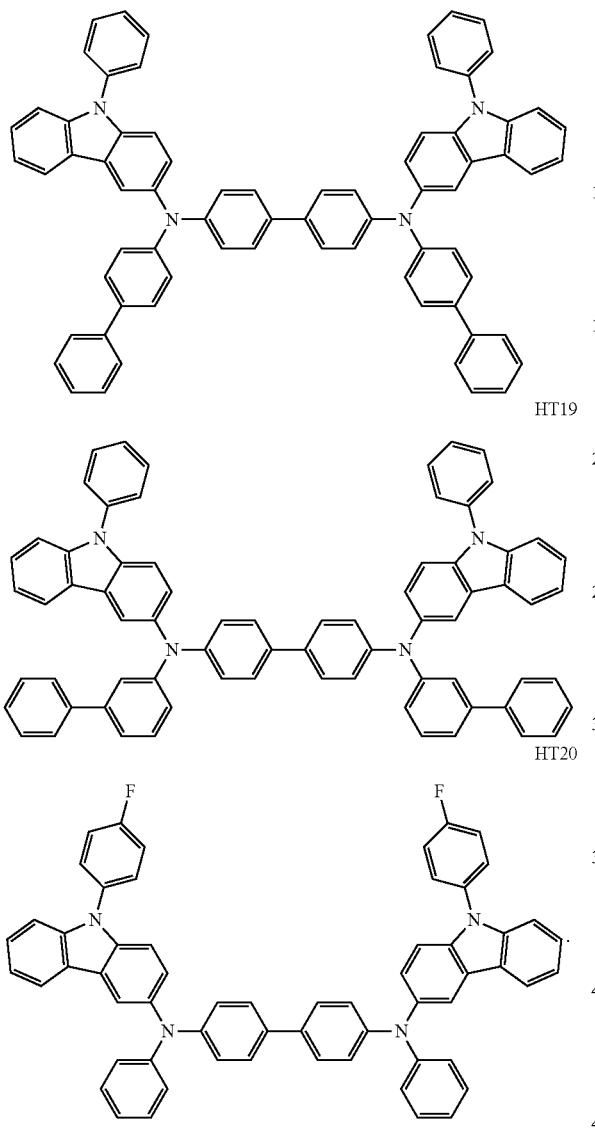

The thickness of the hole transport region may be in a range of about 100 Angstroms (Å) to about 10,000 Å, and in some embodiments, about 100 Å to about 1,000 Å. When the hole transport region includes a hole injection layer and a hole transport layer, the thickness of the hole injection layer may be in a range of about 100 Å to about 10,000 Å, in some embodiments, about 100 Å to about 1,000 Å, the thickness of the hole transport layer may be in a range of about 50 Å to about 2,000 Å, and in some embodiments, about 100 Å to about 1,500 Å. While not wishing to be bound by theory, it is understood that when the thicknesses of the hole transport region, the hole injection layer, and the hole transport layer are within these ranges, excellent hole transport characteristics may be obtained without a substantial increase in driving voltage.

The hole transport region may include a charge-generating material as well as the mentioned materials above, to improve conductive properties. The charge-generating material may be homogeneously or non-homogeneously dispersed throughout the hole transport region.

The charge-generating material may be, for example, a p-dopant. The p-dopant may be selected from a quinone derivative, a metal oxide, and a cyano group-containing compound, but embodiments are not limited thereto. For example, non-limiting examples of the p-dopant may include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1 or HT-D2, but embodiments are not limited thereto:

Compound HT-D1

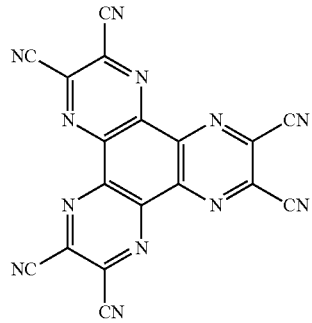

F4-TCNQ

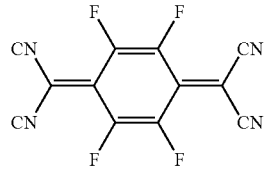

Compound HT-D2

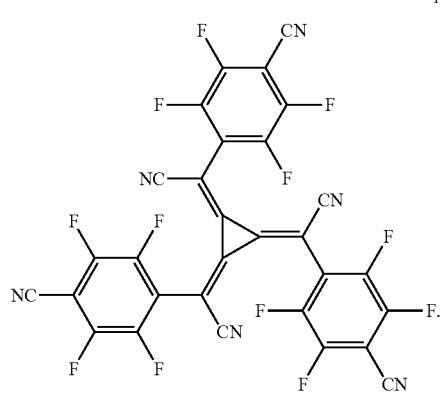

The hole transport region may further include a buffer layer.

The buffer layer may compensate for an optical resonance distance according to a wavelength of light emitted from the emission layer to improve the efficiency of an organic light-emitting device.

The hole transport region may further include an electron blocking layer. The electron blocking layer may include any suitable known material, e.g., mCP, but embodiments are not limited thereto:

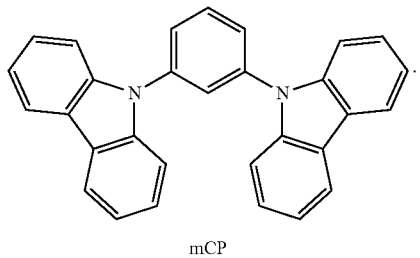 [SMILES: c1cc(-n2c3ccccc3c3ccccc32)cc(-n2c3ccccc3c3ccccc32)c1]

mCP

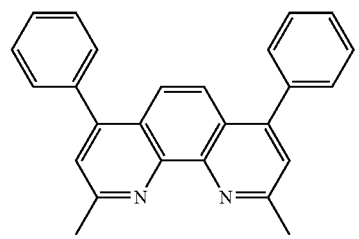

BCP

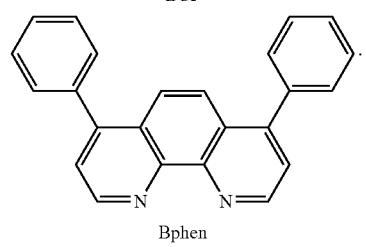

Bphen

The thickness of the electron blocking layer may be in a range of about 50 Å to about 1,000 Å, and in some embodiments, about 70 Å to about 500 Å. While not wishing to be bound by theory, it is understood that when the thickness of the electron blocking layer is within these ranges, excellent electron blocking characteristics may be achieved without a substantial increase in driving voltage.

An emission layer may be formed on the hole transport region by using one or more suitable methods, such as vacuum deposition, spin coating, casting, or an LB method. When the emission layer is formed by vacuum deposition or spin coating, vacuum deposition and coating conditions for the emission layer may be generally similar to the conditions for forming a hole injection layer, though the conditions may vary depending on the compound used.

The emission layer may further include the above-described cross-linked material.

When the organic light-emitting device 10 is a full color organic light-emitting device, the emission layer may be patterned into a red emission layer, a green emission layer, and a blue emission layer. In some embodiments, the emission layer may have a structure in which the red emission layer, the green emission layer, and/or the blue emission layer are layered to emit white light or other various embodiments are possible.

The thickness of the emission layer may be in a range of about 100 Å to about 1,000 Å, and in some embodiments, about 200 Å to about 600 Å. While not wishing to be bound by theory, it is understood that when the thickness of the emission layer is within these ranges, excellent light-emission characteristics may be achieved without a substantial increase in driving voltage.

An electron transport region may be next formed on the emission layer.

The electron transport region may include at least one selected from a hole blocking layer, an electron transport layer, and an electron injection layer, but embodiments not limited thereto.

In some embodiments, the electron transport region may have a structure of a hole blocking layer/an electron transport layer/an electron injection layer or an electron transport layer/an electron injection layer, but embodiments are not limited thereto. The electron transport layer may have a single layer structure or a multi-layer structure including two or more different materials.

The conditions for forming a hole blocking layer, an electron transport layer, and an electron injection layer may be inferred based on the conditions for forming the hole injection layer.

When the electron transport region includes a hole blocking layer, the hole blocking layer, for example, may include at least one of BCP and Bphen, but embodiments are not limited thereto:

A thickness of the hole blocking layer may be in a range of about 20 Å to about 1,000 Å, and in some embodiments, about 30 Å to about 300 Å. While not wishing to be bound by theory, it is understood that when the thickness of the hole blocking layer is within these ranges, excellent hole blocking characteristics may be achieved without a substantial increase in driving voltage.

The electron transport layer may further include at least one selected from BCP, Bphen, Alq$_3$, BAlq, TAZ, and NTAZ:

Alq$_3$

BAlq

-continued
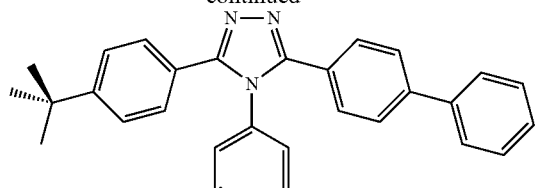
TAZ
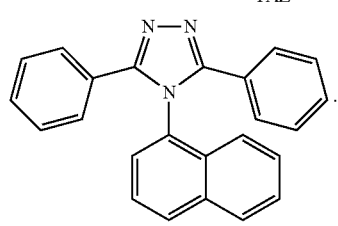
NTAZ
Alternatively, the electron transport layer may include at least one selected from Compounds ET1 to ET19, but embodiments are not limited thereto:
ET1
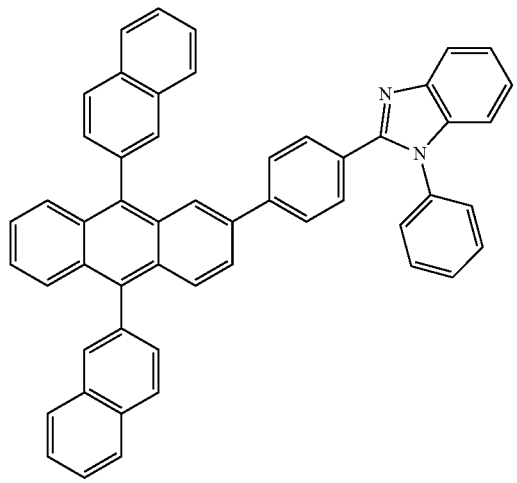
ET2
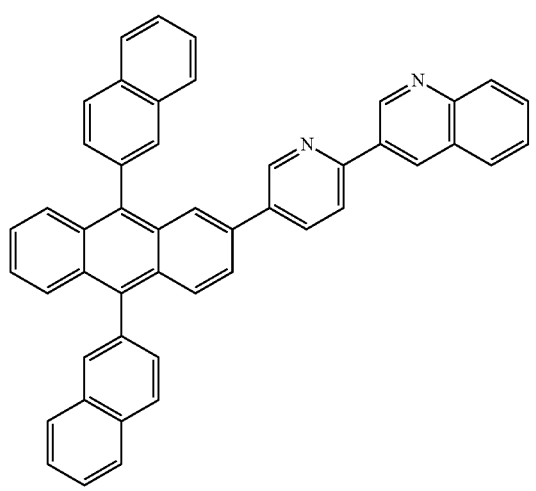
-continued
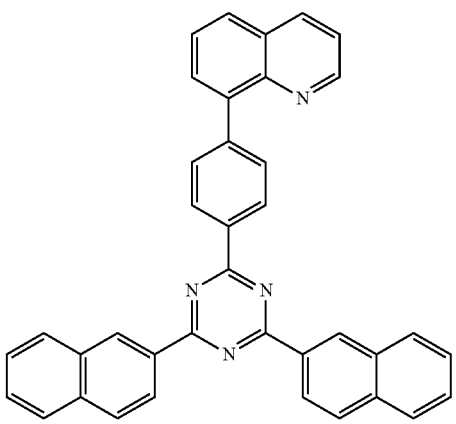
ET3
ET4
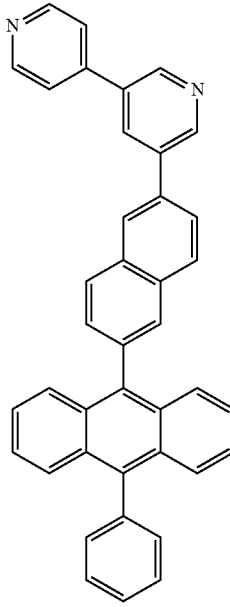
ET5
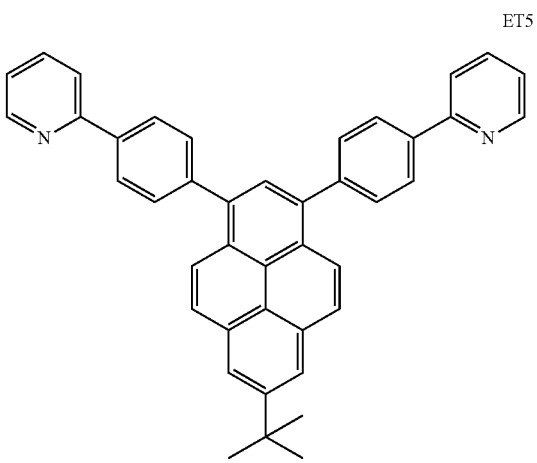

-continued
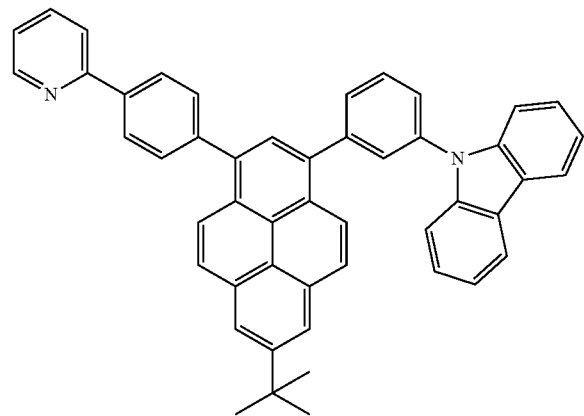
ET6
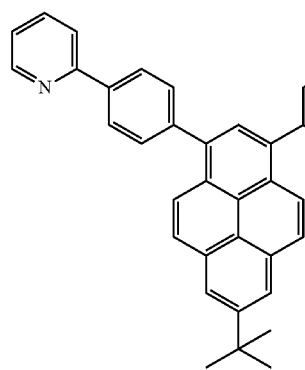
ET7
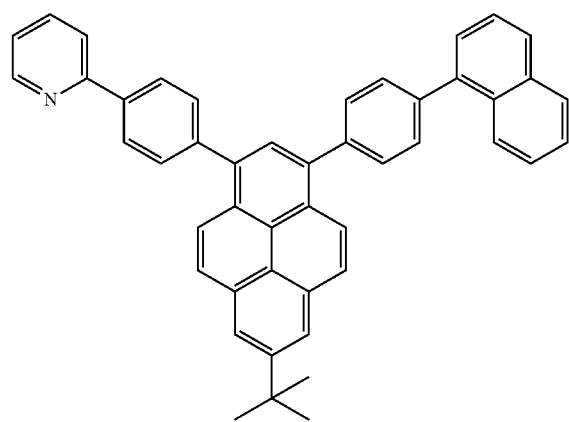
ET8
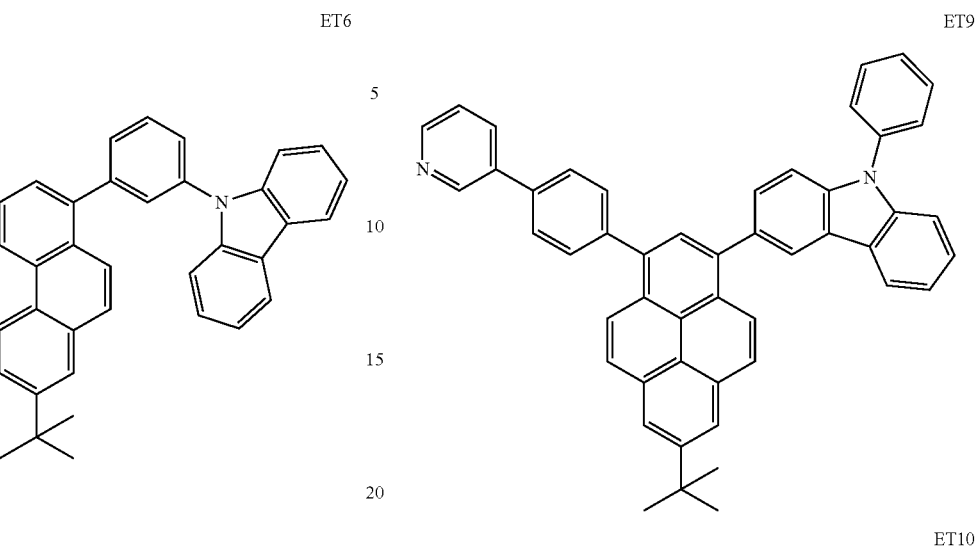
ET9
ET10
ET11
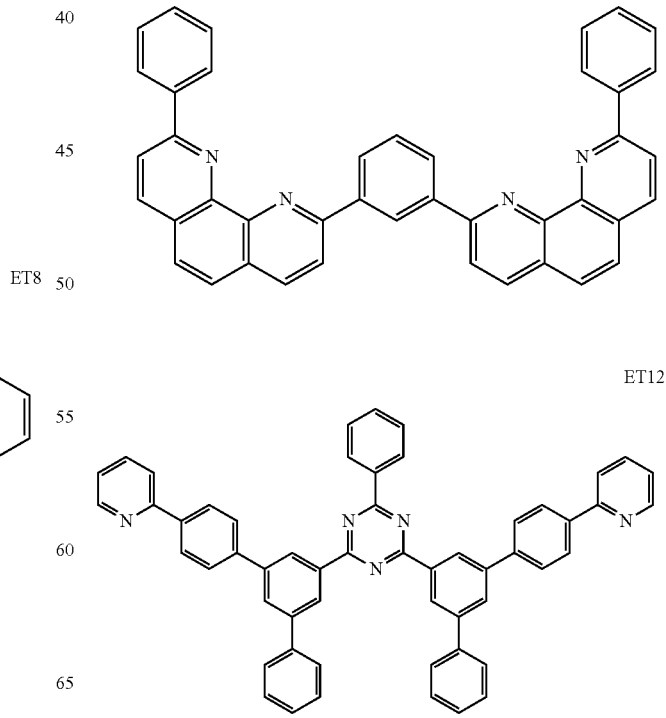
ET12

ET13
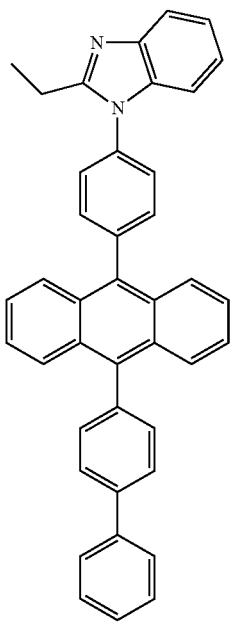
ET16
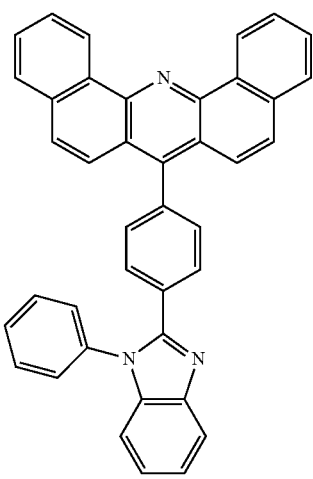
ET17
ET14
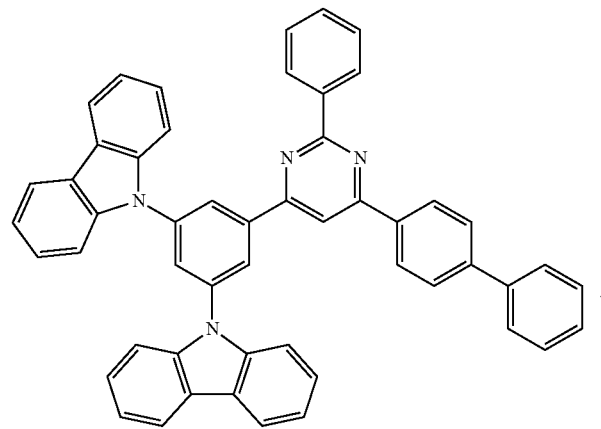
ET15
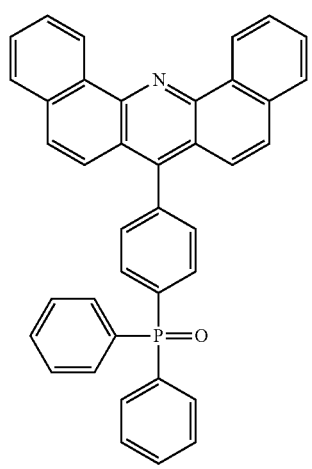
ET18
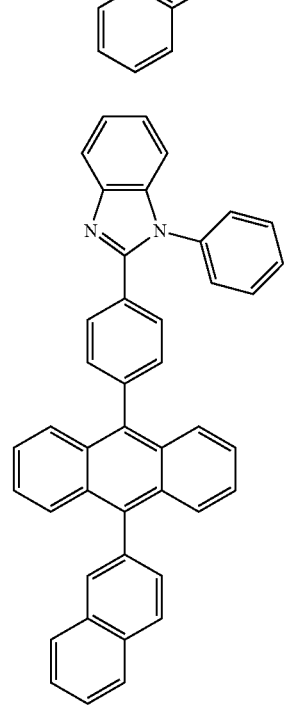

ET19

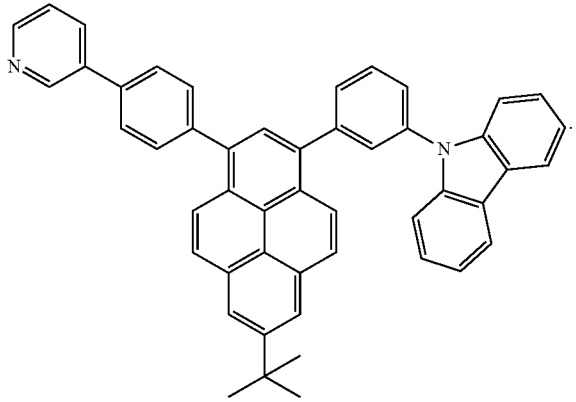

The thickness of the electron transport layer may be in a range of about 100 Å to about 1,000 Å, and in some embodiment, about 150 Å to about 500 Å. While not wishing to be bound by theory, it is understood that when the thickness of the electron transport layer is within these ranges, excellent electron transport characteristics may be achieved without a substantial increase in driving voltage.

The electron transport layer may further include a metal-containing material, in addition to the materials described above.

The metal-containing material may include a Li complex. The Li complex may include, e.g., Compound ET-D1 (lithium quinolate, LiQ) or ET-D2:

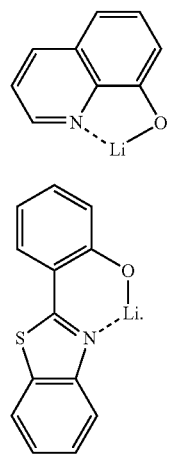

ET-D1

ET-D2

The electron transport region may include an electron injection layer that facilitates electron injection from the second electrode 19.

The electron injection layer may include at least one selected from, LiF, NaCl, CsF. Li$_2$O, and BaO.

The thickness of the electron injection layer may be in a range of about 1 Å to about 100 Å, and in some embodiments, about 3 Å to about 90 Å. While not wishing to be bound by theory, it is understood that when the thickness of the electron injection layer is within these ranges, excellent electron injection characteristics may be achieved without a substantial increase in driving voltage.

The second electrode 19 is on the organic layer 15. The second electrode 19 may be a cathode. A material for the second electrode 19 may be a material having a relatively low work function, such as a metal, an alloy, an electrically conductive compound, and a mixture thereof. Detailed examples of the material for forming the second electrode 19 may include lithium (Li), magnesium (Mg), aluminum (Al), aluminum-lithium (Al—Li), calcium (Ca), magnesium-indium (Mg—In), and magnesium-silver (Mg—Ag). In some embodiments, ITO or IZO may be used to form a transmissive second electrode 19 to manufacture a top emission light-emitting device, and such a variation may be possible.

Hereinbefore the organic light-emitting device 10 has been described with reference to FIG. 1, but embodiments are not limited thereto.

The term "$C_1$-$C_{60}$ alkyl group" as used herein refers to a linear or branched aliphatic hydrocarbon monovalent group having 1 to 60 carbon atoms. Detailed examples thereof are a methyl group, an ethyl group, a propyl group, an iso-butyl group, a sec-butyl group, a tert-butyl group, a pentyl group, an iso-amyl group, and a hexyl group.

The term "$C_1$-$C_{20}$ alkoxy group" as used herein refers to a monovalent group represented by —$OA_{101}$ (where $A_{101}$ is the $C_1$-$C_{20}$ alkyl group). Detailed examples thereof may include a methoxy group, an ethoxy group, and an isopropyloxy group.

The term "$C_1$-$C_{20}$ alkylene group" as used herein refers to a divalent group having the same structure as the $C_1$-$C_{20}$ alkyl group.

The term "$C_1$-$C_{20}$ oxyalkenylene group" as used herein refers to a divalent group having the same structure as the $C_1$-$C_{20}$ alkylene group of which at least one carbon is substituted with oxygen.

The term "$C_1$-$C_{20}$ thioalkenylene group" as used herein refers to a divalent group having the same structure as the $C_1$-$C_{20}$ alkylene group of which at least one carbon is substituted with sulfur.

The term "ambient temperature" or "room temperature" as used herein refers to a temperature of about 25° C.

Hereinafter, an organic light-emitting device 10, according to an embodiment, will be described in detail with reference to Synthesis Examples and Examples; however, the inventive concept is not limited thereto. The wording "B was used instead of A" used in describing Synthesis Examples means that an amount of B used was identical to an amount of A used based on molar equivalence.

EXAMPLE

Synthesis Example 1: Synthesis of Compound DA1, Compound Br6A, and Polymer (1) Synthesis of Compound DA1
Compound DA1 was synthesized according to the following Reaction Scheme 1:
Reaction Scheme 1

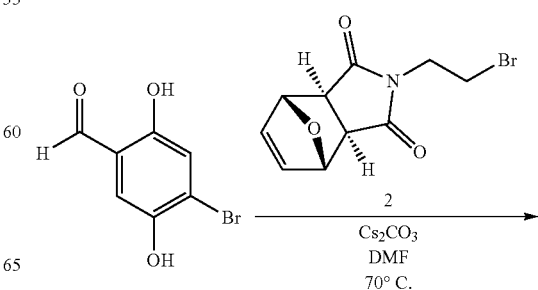

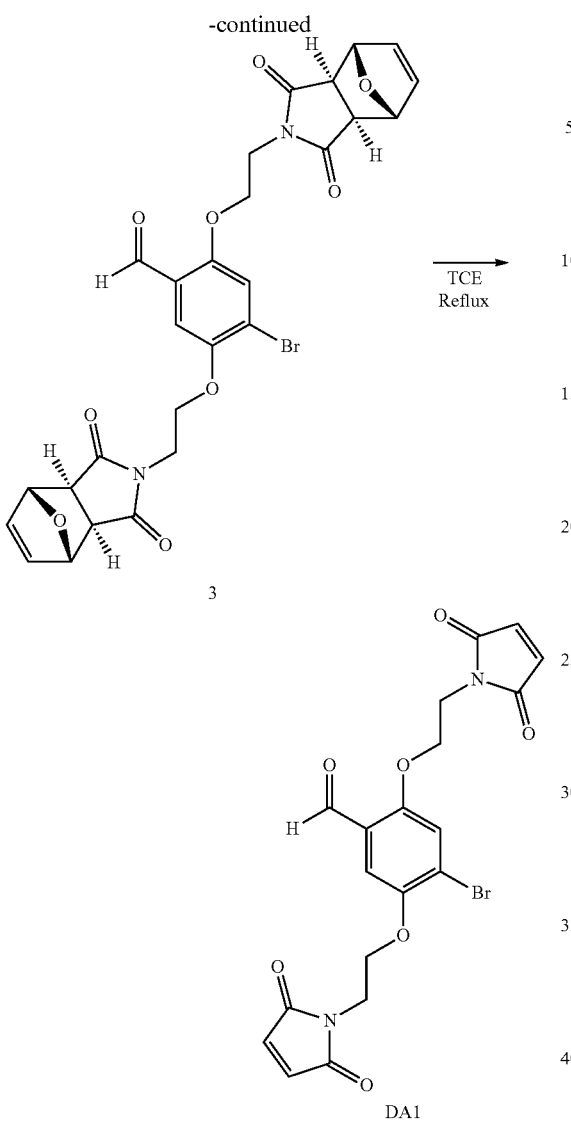

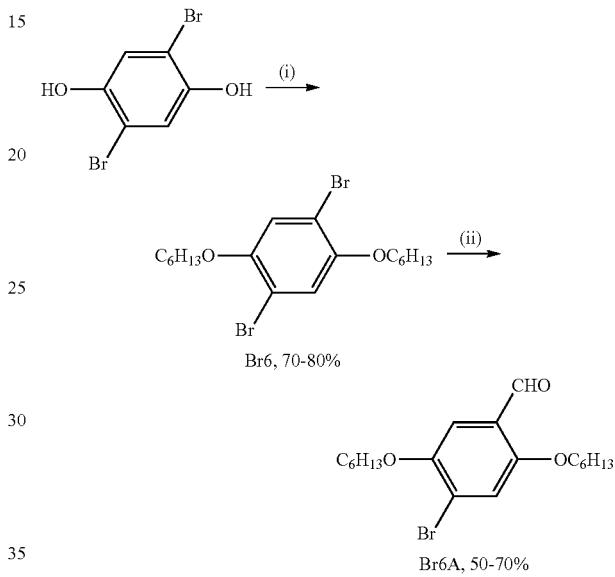

Br6, 70-80%

Br6A, 50-70%

To a solution of 205 milligrams (mg) of Compound 1 (0.94 millimoles, mmol) and 566 mg of Compound 2 (2.08 mmol) in 9.4 ml of dimethylformamide (DMF) was added $Cs_2CO_3$ (677 mg, 2.08 mmol) at room temperature. The solution was stirred at 70° C. for 10 h. After cooling to room temperature, the mixture was poured into 1 molar (M) HCl aqueous solution and extracted with ethyl acetate. The organic layer was separated and washed with water and brine. The washed organic layer was dried over magnesium sulfate ($MgSO_4$), and the solvent was evaporated. The obtained crude product was purified by column chromatography using hexane and acetone at a volume ratio of about 1:1 to thereby obtain Compound 3.

10 ml of tetrachloroethane (TCE) solution of Compound 3 was heated under reflux overnight. After cooling to room temperature, the mixture was purified by column chromatography using hexane and acetone at a volume ratio of about 4:1 to thereby obtaining 67 mg of Compound DA1 (yield 15%) as an off-white solid powder. Compound DA1 was identified using $^1H$ nuclear magnetic resonance (NMR) and high resolution mass spectrometric (HRMS) analyses.

$^1H$ NMR (400 MHz, $CDCl_3$): δ 10.24 (s, 1H), 7.26 (s, 1H), 7.13 (s, 1H), 6.72 (s, 4H), 4.16 (t, 4H, J=5.4 Hz), 3.97 (t, 4H, J=5.4 Hz). $^{13}C$ NMR (100 MHz, $CDCl_3$): δ 188.7, 170.6, 170.5, 155.2, 149.7, 134.5, 134.5, 124.5, 121.0, 118.3, 111.3, 66.3, 66.2, 37.1, 37.0. MS m/z (ESI$^+$, relative intensity): 948 (33), 487 (48), 463 (M$^+$+1, 99), 284 (9), 256 (12), 130 (24), 124 (11).

HRMS (ESI$^+$) calcd. for $C_{19}H_{16}BrN_2O_7$ (M$^+$+1) 463.0141, found 463.0135.

(2) Synthesis of Compound Br6A

Compound Br6A was synthesized according to the following Reaction Scheme 2:

Reaction Scheme 2

(i) Synthesis of Intermediate Br6

2,5-dibromohydroquinone (1 equivalent, equiv.) and 1-bromo-n-alkane (2.1 equiv.) were loaded into a glass flask and dissolved in dimethylformamide to obtain a solution of 2,5-dibromohydroquinone having a concentration of about 1 milliliter (mL) of solvent per gram. Potassium carbonate (3 equiv.) was added to the glass flask and the glass flask was sealed under nitrogen, stirred, and refluxed for 24 hours. The reaction product was then cooled and filtered. The crude product was purified by column chromatography with hexanes. Compound Br6 as white crystals was collected in yields of about 70% to about 80%. Compound Br6 was identified using $^1H$ NMR.

$^1H$ NMR (500 MHz, $CDCl_3$): δ 7.05 (s 2H), 3.91 (t 4H), 1.76 (m 4H), 1.43 (m 4H), 1.33 (m 8H), 0.91 (m 6H).

(ii) Synthesis of Intermediate Br6A

Compound Br6 (1 equiv.) was loaded into a glass flask and vacuum purged with argon three times, Anhydrous tetrahydrofuran was added to the glass flask to prepare a solution having the concentration of about 25 mL of solvent per gram of Br6, and the glass flask placed into a bath of dry ice and 2-propanol. Butyllithium (1 equiv.) is added dropwise to the glass flask and the reaction mixture was stirred at a temperature of about −48° C. for about 1 hour. Anhydrous DMF (4 equiv.) was then added thereto and the reaction was allowed to warm to a temperature of about 23° C. for about 3 hours. The reaction was quenched and extracted with diethyl ether. First purification was carried out by column chromatography using an eluent of ethyl acetate and hexane at a ratio of about 1:30, and then—by recrystallization from methanol and acetonitrile. Intermediate Br6A as white crystals was collected in yields of about 50% to about 70%. Intermediate Br6A was identified using $^1$H NMR.

$^1$H NMR (500 MHz, d6-DMSO): δ 10.29 (s 1H), 7.53 (s 1H), 7.23 (s 1H), 4.09 (t 2H), 4.01 (t 2H), 1.73 (m 4H), 1.42 (m 4H), 1.30 (m 8H), 0.87 (m 6H).

(3) Synthesis of Polymer

Referring to Reaction Scheme 3 and Table 1, polymers (PFMA, P(FMA-r-MMA), P(FMA-r-S), P(FMA-r-NiPAM), P(FMA-r-AM), P(FMA-r-AP), P(FMA-r-AN), and P(FMA-r-VBC)) were synthesized. In addition, it was found that the synthesized polymers had number average molecular weight ($M_n$) and polydispersity index (PDI) as shown in Table 1.

Reaction Scheme 3

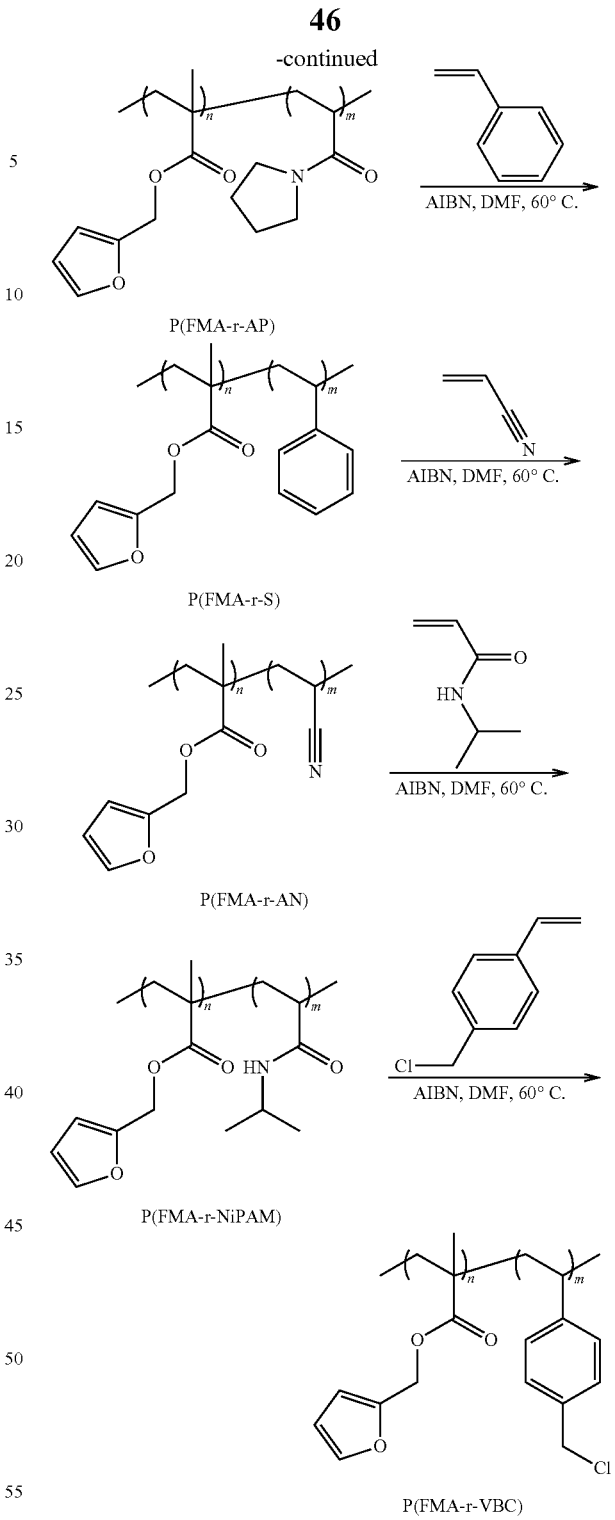

Furfuryl methacrylate (FMA) and comonomer were polymerized via free radical polymerization using azobisisobutyronitrile (AIBN) as the initiator. In the polymerization process, FMA and the comonomer at the specified feed ratio as shown in Table 1, and AIBN were dissolved in DMF. The solution was purged with argon for 30 minutes (min). The monomers/solvent weight ratio was kept at about 30%, and the reaction was carried out at a temperature of about 60° C. The resulting copolymers were precipitated in diethyl ether or methanol and dried under vacuum overnight.

TABLE 1

|  | Feed ratio | | Composition | | $M_n$ | |
| --- | --- | --- | --- | --- | --- | --- |
|  | FMA | Comonomer | FMA | Comonomer | (g/mol) | PDI |
| PFMA (polymer A) | 10 | 0 | 1 | 0 | 145,400 | 2.24 |
| P(FMA-r-MMA) (polymer B-1) | 7 | 3 | 0.618 | 0.382 | 142,700 | 2.01 |
| P(FMA-r-MMA) (polymer B-2) | 3 | 7 | 0.277 | 0.723 | 136,700 | 2.16 |
| P(FMA-r-MMA) (polymer B-3) | 1 | 9 | 0.116 | 0.884 | 138,900 | 2.04 |
| P(FMA-r-S) (polymer C) | 1 | 9 | 0.127 | 0.873 | 34,300 | 1.72 |
| P(FMA-r-NiPAM) (polymer D) | 1 | 9 | 0.116 | 0.884 | 41,600 | 1.99 |
| P(FMA-r-AM) (polymer E) | 1 | 9 | 0.295 | 0.705 | — | — |
| P(FMA-r-AP) (polymer F) | 1 | 9 | 0.268 | 0.732 | 138,500 | 8.87 |
| P(FMA-r-AN) (polymer G) | 1 | 9 | 0.313 | 0.687 | — | — |
| P(FMA-r-VBC) (polymer H) | 1 | 9 | 0.293 | 0.707 | 39,800 | 7.71 |

Evaluation Example 1: UV-Vis Absorption Spectra

Figure 2A:
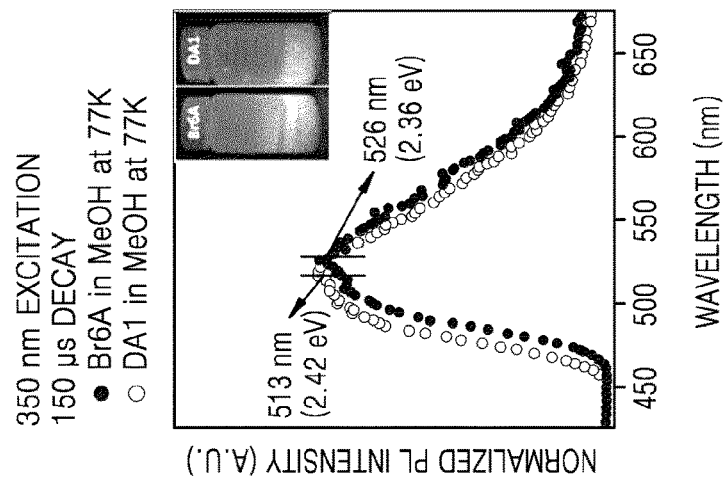
FIG. 2A is a graph of molar extinction coefficient×$10^5$ (reverse molar centimeters) versus wavelength (nanometers, nm) illustrating ultraviolet-visible (UV-Vis) absorption spectra of methanol solutions of Br6A, DA1, M1, and Br6A/M1.

UV-Vis absorption spectra of Compounds Br6A, DA1, M1, and Br6A/M1 in methanol solutions were obtained. The concentration of the methanol solution is as follows, and the results thereof is shown in FIG. 2A. The structure of M1 will be described below.

Concentration of methanol solutions
Br6A: $0.93 \times 10^{-5}$ M
DA1: $1.1 \times 10^{-5}$ M
M1: $2.1 \times 10^{-5}$ M
Br6A/M1: $0.93 \times 10^{-5}$ M/$2.1 \times 10^{-5}$ M

M1

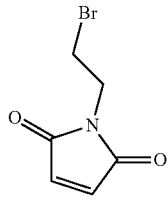

Evaluation Example 2: Evaluation of Emission of Compound (1) Evaluation of Emission at Room Temperature (Fluorescence)

Figure 2B:
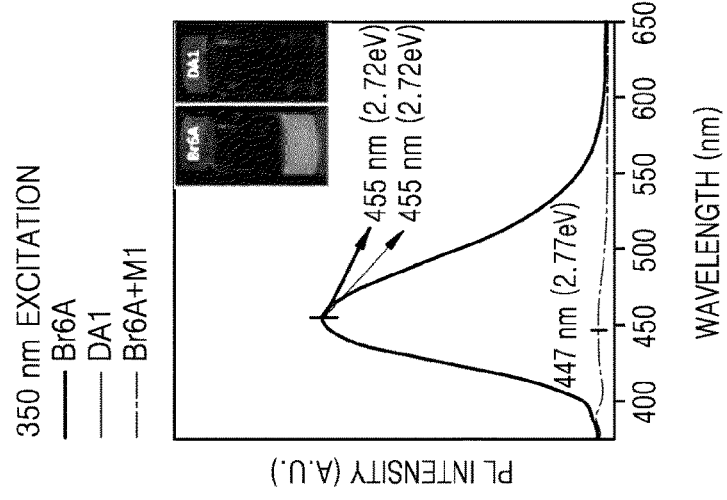
FIG. 2B is a graph of photoluminescent (PL) intensity (arbitrary units, a. u.) versus wavelength (nanometers, nm) illustrating photoluminescence (PL) spectra of methanol solutions of Br6A, DA1, and Br6A/M1.

Photoluminescence (PL) spectra of methanol solutions of Compounds Br6A, DA1, and Br6A/M1, at the same concentrations as those of methanol solutions used in Evaluation Example 1, excited at $\lambda_{ex}$=350 nanometers (nm) were obtained. The results thereof are shown in FIG. 2B. In addition, the inset of FIG. 2B shows PL observation result images of methanol solutions of Compounds Br6A and DA1 at room temperature under ultraviolet light of about 365 nm.

Although Compound Br6A is fluorescent with a quantum yield ($\phi_F$) of about 12% at $\lambda_{max}$=455 nm, Compound DA1 shows negligible fluorescence.

(2) Evaluation of Emission at 77 Kelvins (K) (Phosphorescence)

Figure 2C:
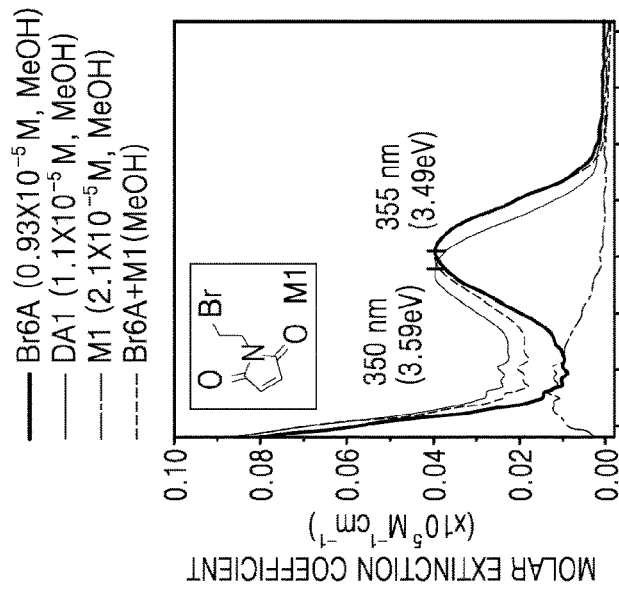
FIG. 2C is a graph of normalized photoluminescent (PL) intensity (arbitrary units, a. u.) versus wavelength (nanometers, nm) illustrating PL spectra of methanol solutions of Br6A and DA1 at 77 Kelvins (K)

PL spectra of methanol solutions of Compounds Br6A, DA1, and Br6A/M1, at the same concentrations as those of methanol solutions used in Evaluation Example 1, excited at $\lambda_{ex}$=350 nm at 77 K were obtained. The results thereof are shown in FIG. 2C. In addition, the inset of FIG. 2C shows PL observation result images of methanol solutions of Compounds Br6A and DA1 at 77 K under ultraviolet light of about 365 nm.

Compounds Br6A and DA1 both showed noticeable phosphorescence.

Synthesis Example 2: Preparation of Compound DA1-doped PFMA(poly(furfuryl methacrylate)) Film 1.0 percent by weight (wt %) of the PFMA (polymer A) obtained in Synthesis Example 1-(3) was dissolved in chloroform (CHCl$_3$) and mixed with Compound DA1 (1.2 wt % of Compound DA1 for polymer A). The mixed solution was drop-cast on a pre-cleaned glass substrate and kept at room temperature for about 10 minutes. The resulting drop-cast film was thermally annealed at a temperature of about 120° C. for about 20 min under nitrogen atmosphere, leading to the formation of covalent bonding between Compound DA1 and Compound PFMA by Diels-Alder reaction.

Comparative Synthesis Example 2-1: Preparation of Compound Br6A-doped PFMA Film

A Compound Br6A-doped PFMA film was prepared in the same manner as in Synthesis Example 2, except that Compound Br6A (1.0 percent by weight (wt %) of Compound Br6A for polymer A) was used instead of Compound DA1.

Comparative Synthesis Example 2-2: Preparation of PFMA Film

A PFMA film was prepared in the same manner as in Synthesis Example 2, except that Compound DA1 was not used.

Evaluation Example 3: Test of Diels-Alder Reaction in Film

Figure 3A:
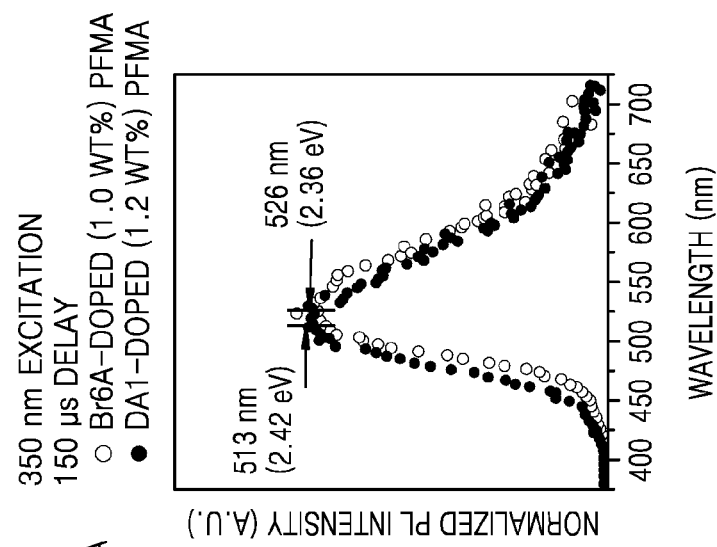
FIG. 3A is a graph of normalized absorption (arbitrary units, a. u.) versus wavelength (nanometers, nm) illustrating UV-Vis absorption spectra of a Compound DA1-doped PFMA film before and after thermal annealing.

In order to confirm the formation of covalent bonding between Compound DA1 and Compound PFMA by Diels-Alder reaction, disappearance of an absorption peak at around 300 nm (a peak corresponding to an nπ* transition of maleimide) in UV-Vis absorption spectra was tested. The results thereof are shown in FIG. 3A.

Figure 3B:
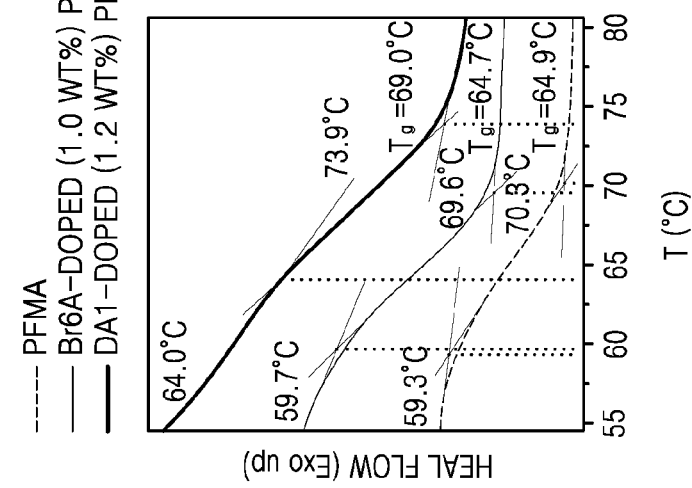
FIG. 3B is a graph of heat flow (exo up) versus temperature (degree Centigrade, ° C.) illustrating differential scanning calorimetry (DSC) curves of a Compound Br6A-doped PFMA film, a Compound DA1-doped PFMA film, and a PFMA film.

Differential scanning calorimetry (DSC) was carried out using the films prepared in Synthesis Example 2 and Comparative Synthesis Examples 2-1 and 2-2. The glass transition temperatures ($T_g$) thereof were measured. The results thereof are shown in FIG. 3B. In consideration of improved $T_g$ of the film prepared in Synthesis Example 2, it was found that the Diels-Alder reaction was successfully occurred. Due to the Diels-Alder reaction, mobility of polymer chains was restricted in the film prepared in Synthesis Example 2, thus increasing $T_g$.

In addition, the degree of conversion of Diels-Alder reaction was estimated by calculating the expected DA1 spectrum after thermal annealing by subtracting the M1 spectrum from DA1 spectrum before thermal annealing. The estimated degree of conversion of Diels-Alder reaction about 95%.

Evaluation Example 4: Film Characteristics Evaluation 1

PL spectra, phosphorescence quantum yield ($\phi_P$) and phosphorescence lifetime($\tau_P$) of the films prepared in Synthesis Example 2 and Comparative Synthesis Example 2-1 were measured at room temperature. The results thereof are shown in FIGS. 3C to 3E.

Figure 3C:
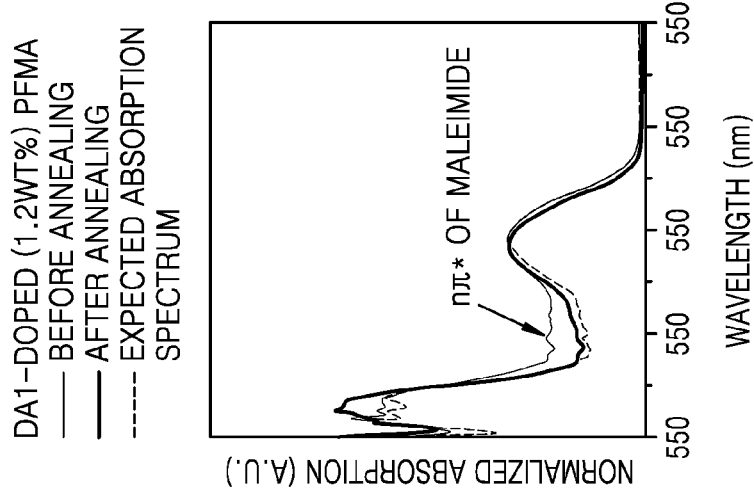
FIG. 3C is a graph of normalized photoluminescent (PL) intensity (arbitrary units, a. u.) versus wavelength (nanometers, nm) illustrating PL spectra of a Compound Br6A-doped PFMA film and a Compound DA1-doped PFMA film.
Figure 3D:
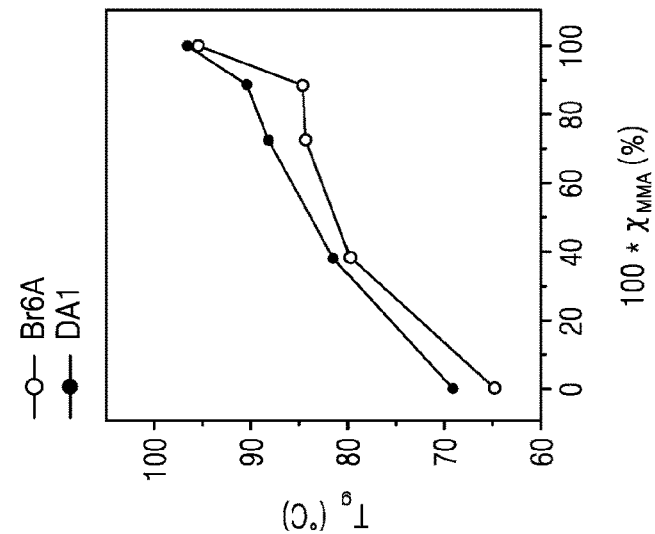
FIG. 3D is a graph of phosphorescence quantum yield $\phi_P$ (percent, %) versus $100*x_{MMA}$ (percent, %) illustrating phosphorescence quantum yield of a Compound Br6A-doped P(FMA-r-MMA) film and a Compound DA1-doped P(FMA-r-MMA) film at different $X_{MMA}$.
Figure 3E:
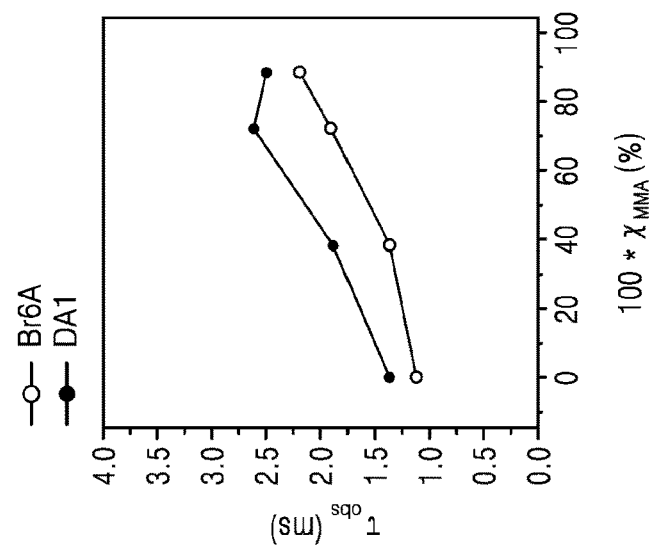
FIG. 3E is a graph of phosphorescence lifetime $\tau_{obs}$ (milliseconds, ms) versus $100*x_{MMA}$ (percent, %) versus $100*x_{MMA}$, (percent, %) illustrating phosphorescence lifetime of a Compound Br6A-doped P(FMA-r-MMA) film and a Compound DA1-doped P(FMA-r-MMA) film at different $x_{MMA}$.

Referring to FIGS. 3C to 3E, the film prepared in Synthesis Example 2 showed phosphorescence at 513 nanometers (nm) (2.42 electron Volts, eV) with lifetime of about 2.6 milliseconds (ms). The film prepared in Comparative Synthesis Example 2-1 showed phosphorescence at 526 nm (2.36 eV) with lifetime of about 2.0 ms.

The observed blue shift of 0.06 eV in the emission spectrum of the film prepared in Synthesis Example 2 was due to the presence of maleimide moieties at the side chain.

Referring to FIG. 3D, $\phi_P$ (13%) of the film prepared in Synthesis Example 2 is about 2.5 times larger than $\phi_P$ (5%) of the film prepared in Comparative Synthesis Example 2-1.

Synthesis Example 3-1: Preparation of Compound DA1-doped P(FMA-r-MMA) Film Having $x_{MMA}$ of about 0.382

The P(FMA-r-MMA) (a random copolymer and a polymer B-1 having $x_{MMA}$ (=number of MMA(s)/number of MMA(s) and FMA(s)) of about 0.382) prepared in Synthesis Example 1-(3) was dissolved in chloroform at a concentration of about 1.0 wt %, and then mixed with Compound DA1 (1.2 wt % of Compound DA1 for polymer B-1), The mixed solution was drop-cast on a pre-cleaned glass substrate and kept at room temperature for about 10 minutes. The resulting drop-cast film was thermally annealed at 120° C. for about 20 minutes under nitrogen atmosphere, leading to the formation of covalent bonding between Compound DA1 and P(FMA-r-MMA) by Diels-Alder reaction.

Synthesis Example 3-2: Preparation of Compound DA1-doped P(FMA-r-MMA) Film Having $x_{MMA}$ of about 0.723

A film was prepared in the same manner as in Synthesis Example 3-1, except that P(FMA-r-MMA) (polymer B-2) having $X_{MMA}$ of about 0.723 was used instead of polymer B-1.

Synthesis Example 3-3: Preparation of Compound DA1-doped P(FMA-r-MMA) Film Having $x_{MMA}$ of About 0.884

A film was prepared in the same manner as in Synthesis Example 3-1 except that P(FMA-r-MMA) (polymer B-3) having $X_{MMA}$ of about 0.884 was used instead of polymer B-1.

Comparative Synthesis Example 3-1: Preparation of Compound Br6A-doped P"F A-r-MMA) Film Having $x_{MMA}$ of about 0.382

A film was prepared in the same manner as in Synthesis Example 3-1, except that Compound Br6A was used (at a concentration of about 1.0 wt % for polymer B-1) instead of Compound DA1.

Comparative Synthesis Example 3-2: Preparation of Compound Br6A-doped P(FMA-r-MMA) Film Having $x_{MMA}$ of about 0.723

A film was prepared in the same manner as in Synthesis Example 3-1 except that polymer B-2 was used instead of polymer B-1, and Compound Br6A was used (at a concentration of about 1.0 wt % for polymer B-2) instead of Compound DA1.

Comparative Synthesis Example 3-3: Preparation of Compound Br6A-doped P(FMA-r-MMA) Film Having $x_{MMA}$ of about 0.884

A film was prepared in the same manner as in Synthesis Example 3-1, except that polymer B-3 was used instead of polymer B-1, and Compound Br6A was used (at a concentration of about 1.0 wt % for polymer B-3) instead of Compound DA1.

Evaluation Example 4: Film Characteristics Evaluation 2

Figure 3F:
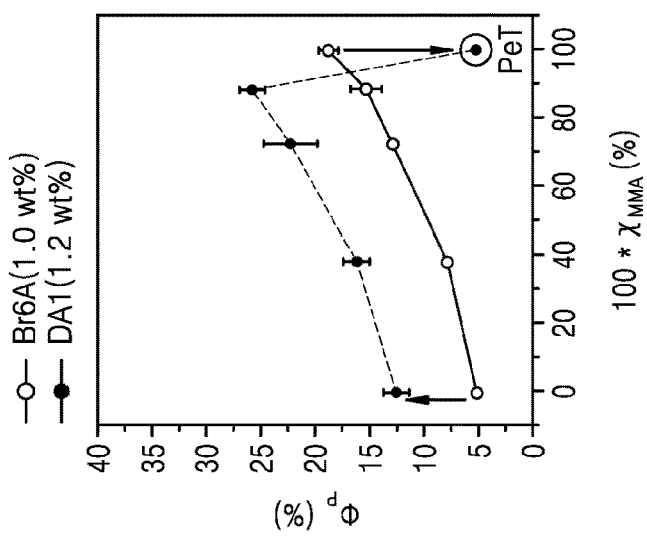
FIG. 3F is a graph of glass transition temperature $T_g$ (degree Centigrade, ° C.) versus $100*x_{MMA}$ (percent, %) illustrating glass transition temperature of a Compound Br6A-doped P(FMA-r-MMA) film and a Compound DA1-doped P(FMA-r-MMA) film at different $x_{MMA}$.

$\phi_P$ and $\tau_P$ of the films prepared in Synthesis Examples 3-1 to 3-3 and Comparative Synthesis Examples 3-1 to 3-3 were measured at room temperature. The results thereof are shown in FIGS. 3D and 3E. Glass transition temperature ($T_g$) of the films prepared in Synthesis Examples 3-1 to 3-3 and Comparative Synthesis Examples 3-1 to 3-3 was measured. The results thereof are shown in FIG. 3F.

Referring to FIGS. 3D and 3E, it was found that as $x_{MMA}$ increases, $\phi_P$ and $\tau_P$ also increase at all $X_{MMA}$, $\phi_P$ of the films prepared in Synthesis Examples 3-1 to 3-3 were found to be about 2 times larger than those of the films prepared in Comparative Synthesis Examples 3-1 to 3-3. $\phi_P$ of the films prepared in Synthesis Example 3-3 were found to reach about 28%, which is comparable to $\phi_P$ of crystals of phosphorescent materials reported in the literature. However, the increased $T_g$ may not fully explain the enhancement of $\phi_P$, because $\phi_P$ of the films prepared in Synthesis Examples 3-2 and 3-3 was higher than that of the film prepared in Comparative Synthesis Example 2-1. This indicates that the molecular motions in the vicinity of phosphors are of high importance.

Figure 4A:
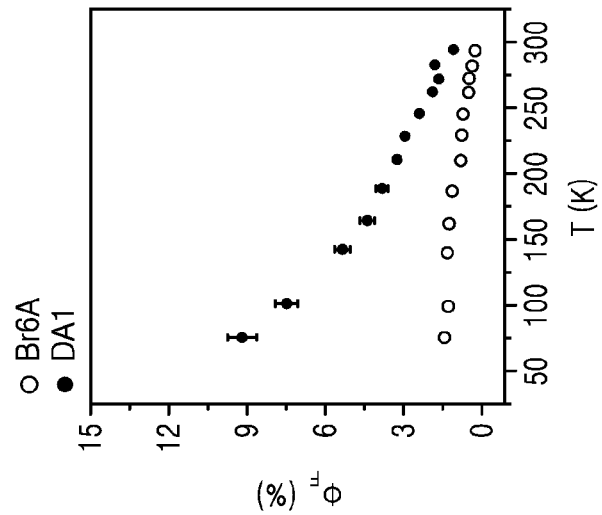
FIG. 4A is a graph of phosphorescence quantum yield $\phi_P$ (percent, %) versus temperature (Kelvin, K), which is a temperature-dependent plot of phosphorescence quantum yield of a Compound Br6A-doped P(FMA-r-MMA) film and a Compound DA1-doped P(FMA-r-MMA) film at $X_{MMA}$ of about 0.88.
Figure 4B:
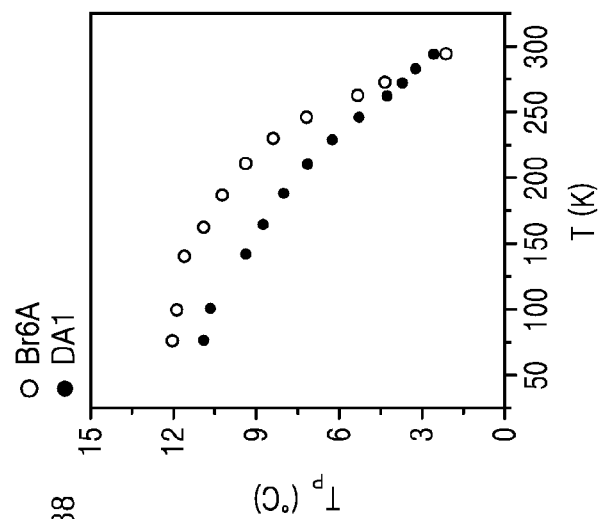
FIG. 4B is a graph of phosphorescence temperature $T_P$ (degree Centigrade, ° C.) versus temperature (Kelvin, K), which is a temperature-dependent plot of phosphorescence lifetime of a Compound Br6A-doped P(FMA-r-MMA) film and a Compound DA1-doped P(FMA-r-MMA) film at $X_{MMA}$ of about 0.88.
Figure 4C:
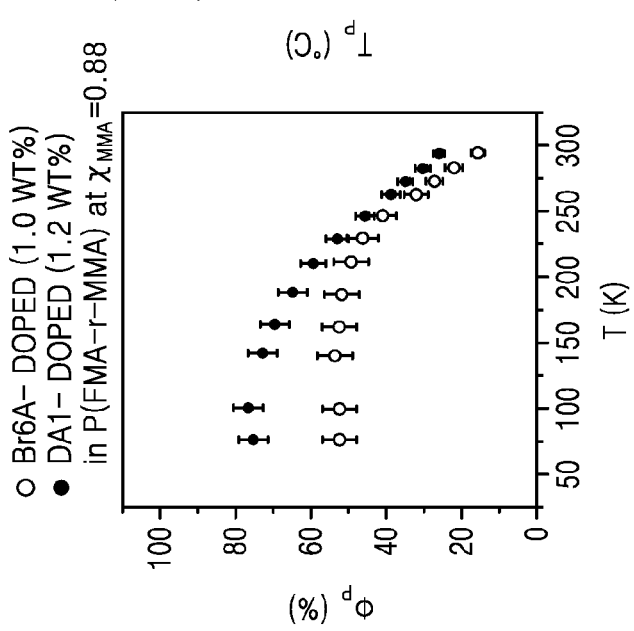
FIG. 4C is a graph of fluorescence quantum yield $\phi_F$ (percent, %) versus temperature (Kelvin, K), which is a temperature-dependent plot of fluorescence quantum yield of a Compound Br6A-doped P(FMA-r-MMA) film and a Compound DA1-doped P(FMA-r-MMA) film at $x_{MMA}$ of about 0.88.
Figure 4D:
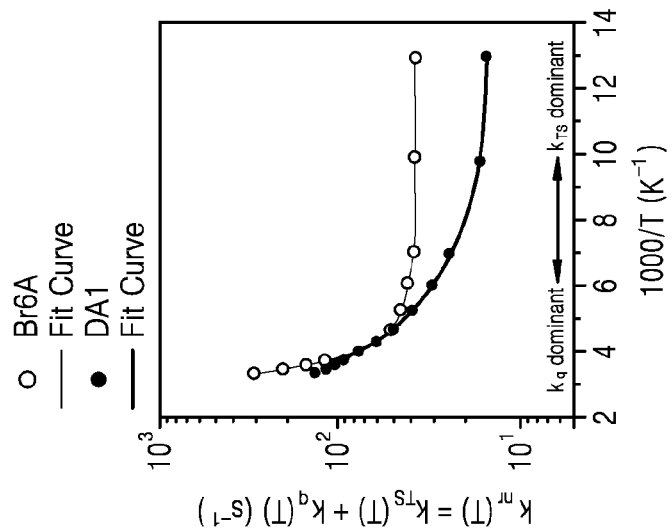
FIG. 4D is a graph of $(1-\phi_F)$ value (percent, %) versus reverse temperature 1,000/T (reverse Kelvins, $K^{-1}$), which is a temperature-dependent plot of a Compound Br6A-doped P(FMA-r-MMA) film and a Compound DA1-doped P(FMA-r-MMA) film at $x_{MMA}$ of about 0.88 for $(1-\phi_F)/\phi_F$.
Figure 4E:
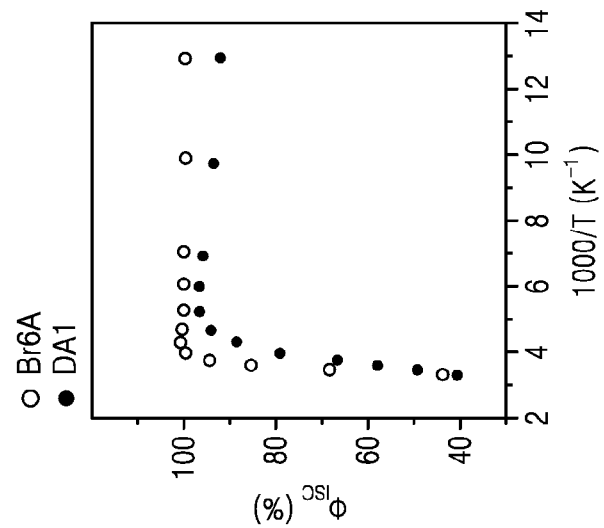
FIG. 4E is a graph of intersystem crossing (ISC) quantum yield $\phi_{ISC}$ (percent, %) versus reverse temperature 1,000/T (reverse Kelvins, $K^{-1}$), which is a temperature-dependent plot of intersystem crossing (ISC) quantum yield of a Compound Br6A-doped P(FMA-r-MMA) film and a Compound DA1-doped P(FMA-r-MMA) film at $x_{MMA}$ of about 0.88.

Evaluation Example 5: Film Characteristics Evaluation 3—Excited State Kinetics Analysis Temperature-dependent measurements of the photoluminescent properties for the films prepared in Synthesis Example 3-3 and Comparative Synthesis Example 3-3 were performed. The results thereof are shown in FIGS. 4A to 4C. To obtain the quantum efficiency for ISC from $S_1$ to $T_n$ ($\phi_{ISC}$), the value of $(1-\phi_F)/\phi_F$ for the films is plotted as a function of temperature. The plot is shown in FIG. 4D. $\phi_{ISC}$, may be determined at a given temperature based on Equation 1. The plot is shown in FIG. 4E.

$$\Phi_{ISC}(T) = \frac{1 - \Phi_F(T)}{1 + (k_{IC}(T)/k_{ISC}(T))} \quad \text{Equation 1}$$

Figure 4F:
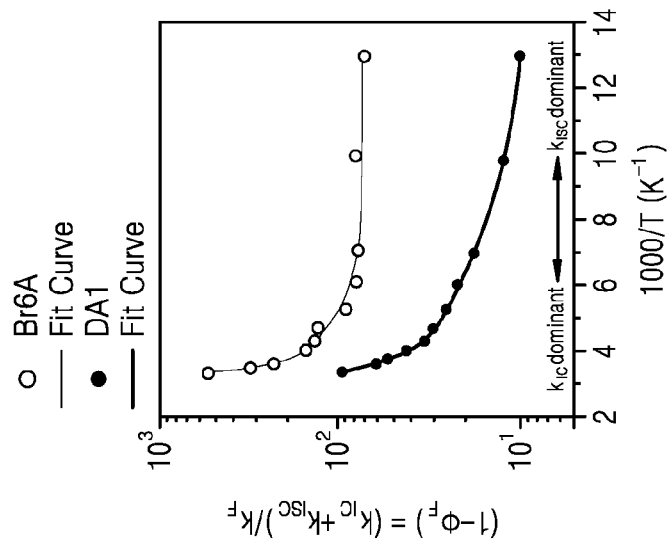
FIG. 4F is a graph of non-radiative decay rate $k_{nr}(T)$ (reverse seconds, $s^{-1}$) versus reverse temperature 1,000/T (reverse Kelvins, $K^{-1}$), which is a graph illustrating non-radiative decay rates of a Compound Br6A-doped P(FMA-r-MMA) film and a Compound DA1-doped P(FMA-r-MMA) film at $X_{MMA}$ of about 0.88 versus 1,000/T.

Based on the obtained $\phi_{ISC}$, the rate constants for phosphorescence process ($k_P$) and non-radiative decay process ($k_{nr}$) were then obtained through Equations 2 and 3. The results thereof are shown in FIG. 4F.

$$k_P(T) = \frac{\Phi_P(T)}{\Phi_{ISC}(T) \cdot \tau_P(T)} \quad \text{Equation 2}$$

$$k_{nr}(T) = \frac{1}{\tau_P(T)} - k_P(T) \quad \text{Equation 3}$$

$k_{nr}$ (143.5 reverse seconds, s$^{-1}$) of the film prepared in Synthesis Example 3-3 at room temperature was significantly small, as compared with $k_{nr}$ (308.0 s$^{-1}$) of the film prepared in Comparative Synthesis Example 3-3 at room temperature, indicating that the enhancement of $\phi_P$ by crosslinking is mainly due to the suppression of the non-radiative decay pathways.

The non-radiative decay for the films prepared in Synthesis Example 3-3 and Comparative Synthesis Example 3-3 are plotted as a function of temperature. The results thereof are shown in FIG. 4F.

Figure 5A:
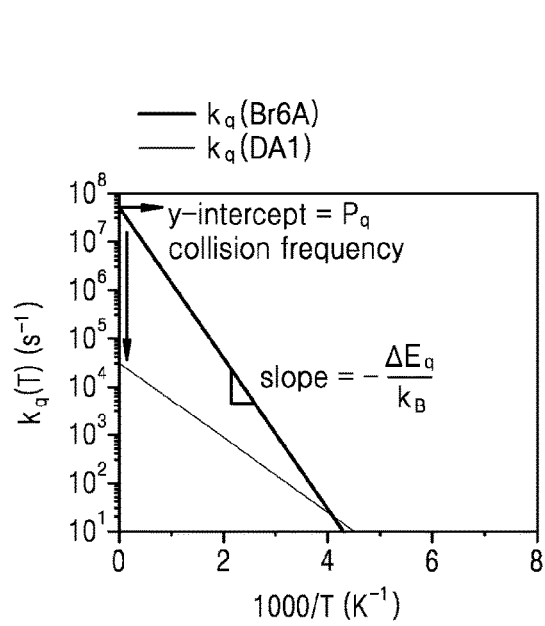
FIG. 5A is a graph of $k_q(T)$ (reverse seconds, $s^{-1}$) versus reverse temperature 1,000/T (reverse Kelvins, $K^{-1}$), illustrating $k_q$ extracted from FIG. 4F versus 1000/T.
Figure 5B:
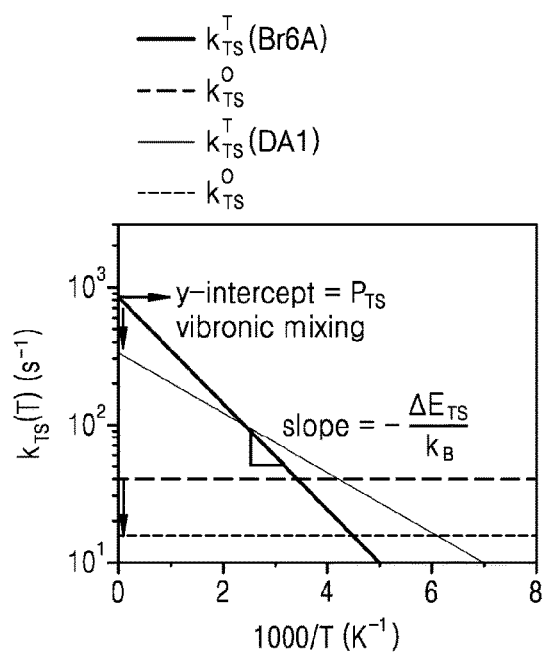
FIG. 5B is a graph of $k_{TS}(T)$ (reverse seconds, $s^{-1}$) versus reverse temperature 1,000/T (reverse Kelvins, $K^{-1}$), illustrating $k_{TS}^T$ and $k_{TS}^0$ extracted from FIG. 4F versus 1,000/T.

Extraction of the rate constant for ISG from $T_1$ to $S_0$ ($k_{TS}$) and the rate constant for an embedded phosphor by interaction with the host matrix and/or oxygen were performed based on Equations 4 to 6.

$$k_{nr}(T) = k_q(T) + k_{TS}(T) \quad \text{Equation 4}$$

$$k_q(T) = P_q \cdot e^{-\Delta E_q/k_B T} \quad \text{Equation 5}$$

$$k_{TS}(T) = k_{TS}^T + k_{TS}^0 = P_{TS} \cdot e^{-\Delta E_{TS}/k_B T} + k_{TS}^0 \quad \text{Equation 6}$$

wherein in Formulae 4 to 6,
$k_{TS}^T$ may be the rate constant for temperature-dependent ISC from $T_1$ to $S_0$,
$k_{TS}^0$ may be the rate constant for temperature-independent ISC from $T_1$ to $S_0$,
$P_q$ may be a pre-exponential factor,
$\Delta E_q$ may be activation energy of quenching processes,
$P_{TS}$ may be the pre-exponential factor of ISC from $T_1$ to $S_0$,
$\Delta E_{TS}$ may be activation energy of temperature-dependent ISC from $T_1$ to $S_0$, and
$k_B$ may be Boltzmann constant.

kq (65.7 s$^{-1}$) of the film prepared in Synthesis Example 3-3 at room temperature was about 3.4 times smaller than $k_q$ (223.5 s$^{-1}$) of the film prepared in Comparative Synthesis Example 3-3 at room temperature. The results thereof are shown in FIG. 5A. Accordingly, it was found that the restriction of diffusion/translational motion of phosphors and of polymer chains effectively suppresses triplet energy transition (ET) process.

Synthesis Examples 4-1 to 4-6: Preparation of Compound DA1-doped Copolymer Films Films according to Synthesis Examples 4-1 to 4-6 were prepared in the same manner as in Synthesis Example 3-1, except that copolymers shown in Table 2 were used instead of polymer B-1.

TABLE 2

| | Used copolymers (P(FMA-r-monomer A) | $x_{monomer\ A}$ |
|---|---|---|
| Synthesis Example 4-1 | P(FMA-r-S) (polymer C) | 0.873 |
| Synthesis Example 4-2 | P(FMA-r-NiPAM) (polymer D) | 0.884 |
| Synthesis Example 4-3 | P(FMA-r-AM) (polymer E) | 0.705 |
| Synthesis Example 4-4 | P(FMA-r-AP) (polymer F) | 0.732 |
| Synthesis Example 4-5 | P(FMA-r-AN) (polymer G) | 0.687 |
| Synthesis Example 4-8 | P(FMA-r-VBC) (polymer H) | 0.707 |

Here, $X_{monomer\ A}$ represents the amount of other monomers other than FMA, as S in P(FMA-r-S). $x_{monomer\ A}$ is calculated by number of monomer A /number of monomer A and FMA.

Comparative Synthesis Examples 4-1 to 4-6: Preparation of Compound Br6A-doped Copolymer Films Films according to Comparative Synthesis Examples 4-1 to 4-6 were prepared in the same manner as in Synthesis Example 4-1, except that copolymers shown in Table 3 were used instead of polymer B-1.

TABLE 3

| | Used copolymers (P(FMA-r-monomer A) | $x_{monomer\ A}$ |
|---|---|---|
| Comparative Synthesis Example 4-1 | P(FMA-r-S) (polymer C) | 0.873 |
| Comparative Synthesis Example 4-2 | P(FMA-r-NiPAM) (polymer D) | 0.884 |
| Comparative Synthesis Example 4-3 | P(FMA-r-AM) (polymer E) | 0.705 |
| Comparative Synthesis Example 4-4 | P(FMA-r-AP) (polymer F) | 0.732 |
| Comparative Synthesis Example 4-5 | P(FMA-r-AN) (polymer G) | 0.687 |
| Comparative Synthesis Example 4-6 | P(FMA-r-VBC) (polymer H) | 0.707 |

Here, $x_{monomer\ A}$ represents the amount of other monomers other than FMA, as S in P(FMA-r-S). $x_{monomer\ A}$ is calculated by number of monomer A /number of monomer A and FMA.

Evaluation Example 6: Film Characteristics Evaluation 4

$\phi_P$ of the films prepared in Synthesis Examples 4-1 to 4-6 and Comparative Synthesis Examples 4-1 to 4-6 were measured at room temperature. The results thereof are shown in FIG. 6.

Figure 6:
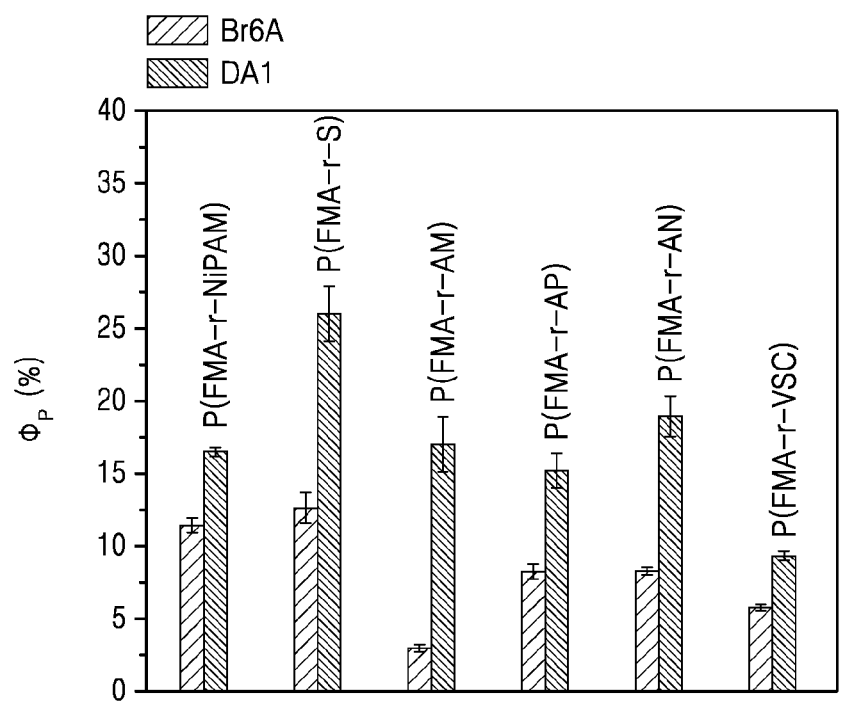
FIG. 6 is a diagram illustrating phosphorescence quantum yield $\phi_P$ (percent, %) of various Compound DA1-doped copolymers and Br6A-doped copolymers.

Referring to FIG. 6, the films prepared in Synthesis Examples 4-1 to 4-6 were found to have improved $\phi_P$, compared with the films prepared in Comparative Synthesis Example 4-1 to 4-6, respectively. Accordingly, it was found that the method of coupling the compound for an organic light-emitting device according to one or more embodiments by covalent linkage may be applied to other polymers as well.

Since the compound for an organic light-emitting device includes at least one cross-linking group, an organic light-emitting device using a cross-linked material thereof may have high efficiency.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. A compound for an organic light-emitting device represented by Formula 1:

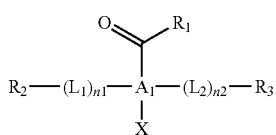

Formula 1 wherein, in Formula 1,
$A_1$ is selected from an aromatic group and an aromatic group having extended $\pi$-conjugation,
$R_1$ is selected from hydrogen and a $C_1$-$C_{60}$ alkyl group,
$L_1$ and $L_2$ are each independently selected from —O—, —S—, a $C_1$-$C_{20}$ alkylene group, a $C_1$-$C_{20}$ oxyalkylene group, and a $C_1$-$C_{20}$ thioalkylene group; and
a $C_1$-$C_{20}$ alkylene group, a $C_1$-$C_{20}$ oxyalkylene group, and a $C_1$-$C_{20}$ thioalkylene group, each substituted with at least one selected from a $C_1$-$C_{20}$ alkyl group and a $C_1$-$C_{20}$ alkoxy group,
n1 and n2 are each independently selected from 0, 1, 2, 3, 4, and 5,
$R_2$ and $R_3$ are each independently selected from hydrogen and a first cross-linking group, provided that at least one of $R_2$ and $R_3$ is the first cross-linking group, and
X is selected from —F, —Cl, —Br, and —I.

2. The compound of claim 1, wherein the first cross-linking group comprises at least one carbon-carbon double bond.

3. The compound of claim 1, wherein the first cross-linking group comprises a substructure represented by one of Formulae 3-1 and 3-2:

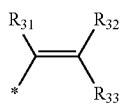

3-1

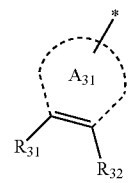

3-2 wherein, in Formulae 3-1 and 3-2,
$A_{31}$ is selected from a $C_5$-$C_{10}$ carbocyclic group and a $C_1$-$C_{10}$ heterocyclic group; and
a $C_5$-$C_{10}$ carbocyclic group and a $C_1$-$C_{10}$ heterocyclic group, each substituted with at least one selected from —F, —Cl, —Br, —I, —C(=O)—, a cyano group, a nitro group, a $C_1$-$C_{20}$ alkyl group, and a $C_1$-$C_{20}$ alkoxy group,
$R_{31}$ to $R_{33}$ are each independently selected from hydrogen, —F, —Cl, —Br, —I, —C(=O)—, a cyano group, a nitro group, a $C_1$-$C_{20}$ alkyl group, and a $C_1$-$C_{20}$ alkoxy group, and
* indicates a binding site to an adjacent atom.

4. The compound of claim 1, wherein
the first cross-linking group is selected from a vinyl group, a maleimide group, a styrene group, and an acrylate group; and
a vinyl group, a maleimide group, a styrene group, and an acrylate group, each substituted with at least one selected from —F, —Cl, —Br, —I, —C(=O)—, a cyano group, a nitro group, a $C_1$-$C_{20}$ alkyl group, and a $C_1$-$C_{20}$ alkoxy group.

5. The compound of claim 1, wherein the first cross-linking group is selected from groups represented by one of Formulae 3-11 to 3-14:

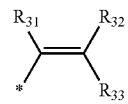

3-11

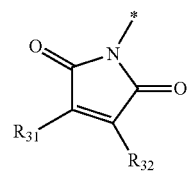

3-12

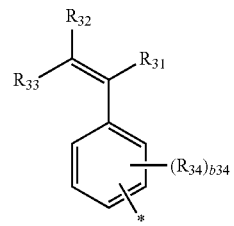

3-13

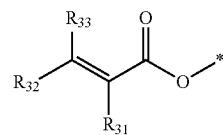

3-14 wherein, in Formulae 3-11 to 3-14,

R$_{31}$ to R$_{34}$ are each independently selected from hydrogen, —F, —Cl, —Br, —I, —C(=O)—, a cyano group, a nitro group, a C$_1$-C$_{20}$ alkyl group, and a C$_1$-C$_{20}$ alkoxy group, and

* indicates a binding site to an adjacent atom.

6. The compound of claim 1, wherein A$_1$ is selected from a phenyl group and a naphthyl group.

7. The compound of claim 1, wherein R$_1$ is hydrogen.

8. The compound of claim 1, wherein L$_1$ and L$_2$ are each independently selected from —O— and a C$_1$-C$_{20}$ alkylene group.

9. The compound of claim 1, wherein R$_2$ and R$_3$ are each independently selected from hydrogen and groups represented by Formulae 3-11 to 3-14, provided that at least one of R$_2$ and R$_3$ is selected from groups represented by Formulae 3-11 to 3-14:

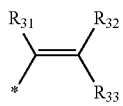
3-11

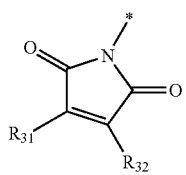
3-12

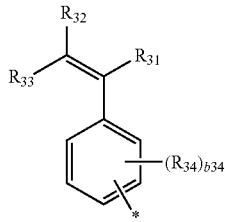
3-13

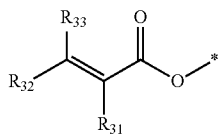
3-14 wherein, in Formulae 3-11 to 3-14,

R$_{31}$ to R$_{34}$ are each independently selected from hydrogen, —F, —Cl, —Br, —I, —C(=O)—, a cyano group, a nitro group, a C$_1$-C$_{20}$ alkyl group, and a C$_1$-C$_{20}$ alkoxy group, and b34 is selected from 1, 2, 3, and 4, and

* indicates a binding site to an adjacent atom.

10. The compound of claim 1, wherein R$_2$ and R$_3$ are each the first cross-linking group.

11. The compound of claim 1, wherein X is —Br.

12. The compound of claim 1, wherein the compound for an organic light-emitting device is represented by Compound DA1:

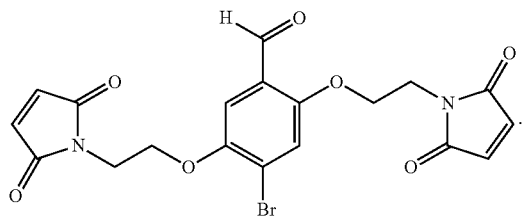
DA1

13. A cross-linked material of a compound for an organic light-emitting device represented by Formula 1 and a polymer:

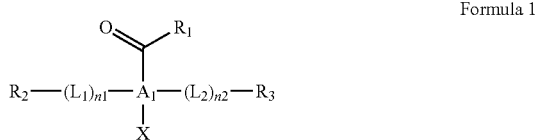
Formula 1 wherein, in Formula 1,

A$_1$ is selected from an aromatic group and an aromatic group having extended π-conjugation, R$_1$ is selected from hydrogen and a C$_1$-C$_{60}$ alkyl group, L$_1$ and L$_2$ are each independently selected from —O—, —S—, a C$_1$-C$_{20}$ alkylene group, a C$_1$-C$_{20}$ oxyalkylene group, and a C$_1$-C$_{20}$ thioalkylene group, n$_1$ and n$_2$ are each independently selected from 0, 1, 2, 3, 4, and 5, R$_2$ and R$_3$ are each independently selected from hydrogen and a first cross-linking group, provided that at least one of R$_2$ and R$_3$ is the first cross-linking group, and X is selected from —F, —Cl, —Br, and —I.

14. The cross-linked material of claim 13, wherein the cross-linked material comprises a constituent unit represented by one of Formulae 2-1 to 2-3:

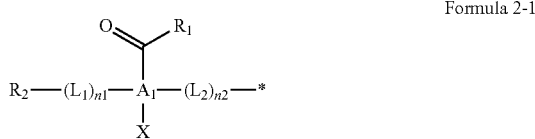
Formula 2-1

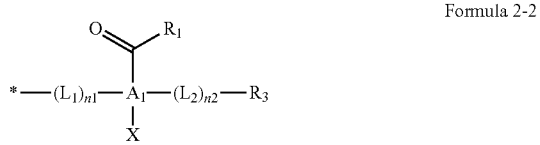
Formula 2-2

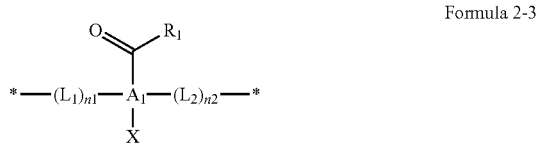
Formula 2-3 wherein, in Formulae 2-1 to 2-3,

A$_1$ is selected from an aromatic group and an aromatic group having extended π-conjugation, R$_1$ is selected from hydrogen and a C$_1$-C$_{60}$ alkyl group, L$_1$ and L$_2$ are each independently selected from —O—, —S—, a C$_1$-C$_{20}$ alkylene group, a C$_1$-C$_{20}$ oxyalkylene group, and a C$_1$-C$_{20}$ thioalkylene group, $n_1$ and $n_2$ are each independently selected from 0, 1, 2, 3, 4, and 5, $R_2$ and $R_3$ are each independently selected from hydrogen and a first cross-linking group, provided that at least one of $R_2$ and $R_3$ is the first cross-linking group, X is selected from —F, —Cl, —Br, and —I, and

* indicates a binding site to an adjacent atom.

15. The cross-linked material of claim 13, wherein the polymer comprises a repeating unit (1) represented by Formula 4:

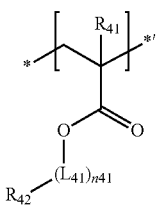

Formula 4 wherein, in Formula 4, $L_{41}$ is selected from —O—, —S—, a $C_1$-$C_{20}$ alkylene group, a $C_1$-$C_{20}$ oxyalkylene group, and a $C_1$-$C_{20}$ thioalkylene group; and a $C_1$-$C_{20}$ alkylene group, a $C_1$-$C_{20}$ oxyalkylene group, and a $C_1$-$C_{20}$ thioalkylene group, each substituted with at least one selected from a $C_1$-$C_{20}$ alkyl group and a $C_1$-$C_{20}$ alkoxy group, $n_{41}$ is selected from 0, 1, 2, 3, 4, and 5, $R_{41}$ is selected from hydrogen, a $C_1$-$C_{20}$ alkyl group, and a $C_1$-$C_{20}$ alkoxy group, $R_{42}$ is a second cross-linking group, and

* and *' each indicate a binding site to an adjacent atom.

16. The cross-linked material of claim 13, wherein the polymer comprises a repeating unit (1) selected from repeating units represented by Formulae 4-11 and 4-12:

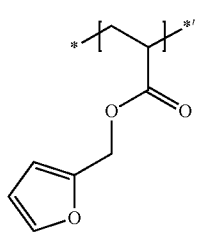

4-11

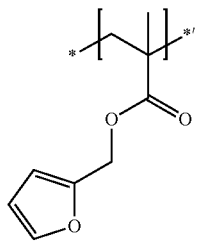

4-12 wherein, in Formulae 4-11 and 4-12,

* and *' each indicate a binding site to an adjacent atom.

17. The cross-linked material of claim 13, wherein the polymer comprises a repeating unit (2) selected from repeating units represented by Formulae 6-1 to 6-4:

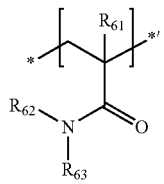

6-1

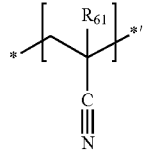

6-2

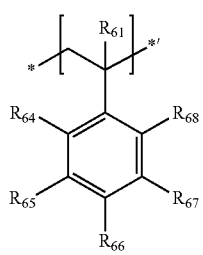

6-3

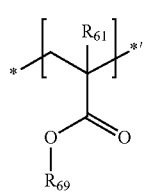

6-4 wherein, in Formulae 6-1 to 6-4, $R_{61}$ is selected from hydrogen, a $C_1$-$C_{20}$ alkyl group, and a $C_1$-$C_{20}$ alkoxy group, $R_{62}$ to $R_{69}$ are each independently selected from hydrogen, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from —F, —Cl, —Br, —I, —C(=O)—, a cyano group, and a nitro group, $R_{62}$ and $R_{63}$ are optionally bound to each other to form a ring, and

* and *' each indicate a binding site to an adjacent atom.

18. The cross-linked material of claim 13, wherein the polymer comprises a repeating unit (2) selected from repeating units represented by Formulae 6-21 to 6-34:

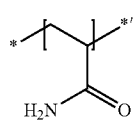

6-21

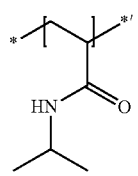

6-22

6-23 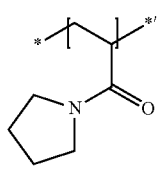

6-24 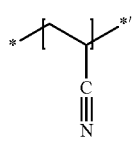

6-25 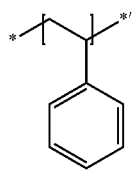

6-26 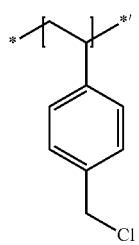

6-27 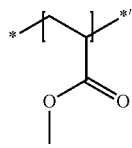

6-28 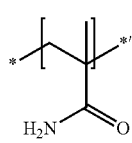

6-29 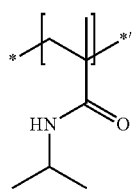

6-30 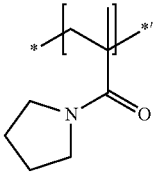

6-31 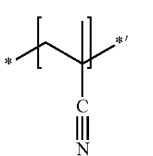

6-32 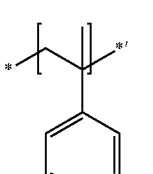

6-33 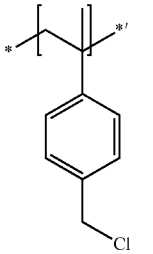

6-34 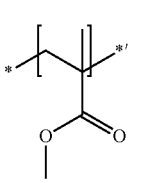

wherein, in Formulae 6-21 and 6-34,
* and *' each indicate a binding site to an adjacent atom.

19. An organic light-emitting device comprising:
a first electrode;
a second electrode; and
an organic layer disposed between the first electrode and the second electrode,
wherein the organic layer comprises an emission layer and at least one cross-linked material of claim 13.

20. The organic light-emitting device of claim 19, wherein the emission layer comprises the at least one cross-linked material.

* * * * *